us010154911B2

(12) United States Patent
Predick et al.

(10) Patent No.: US 10,154,911 B2
(45) Date of Patent: Dec. 18, 2018

(54) EXPANDABLE IMPLANT ASSEMBLY

(71) Applicant: Life Spine, Inc., Huntley, IL (US)

(72) Inventors: Daniel Predick, Chicago, IL (US); Madeline Wolters, Carol Stream, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/645,179

(22) Filed: Jul. 10, 2017

(65) Prior Publication Data

US 2017/0367842 A1 Dec. 28, 2017

Related U.S. Application Data

(63) Continuation-in-part of application No. 14/714,821, filed on May 18, 2015, now Pat. No. 9,801,733, (Continued)

(51) Int. Cl.
*A61F 2/44* (2006.01)
*A61B 17/88* (2006.01)
*A61F 2/30* (2006.01)

(52) U.S. Cl.
CPC ........ *A61F 2/4425* (2013.01); *A61B 17/8858* (2013.01); *A61F 2/44* (2013.01); (Continued)

(58) Field of Classification Search
CPC . A61B 17/68; A61B 17/70; A61F 2/44; A61F 2/442; A61F 2/4425; A61F 2/4455
See application file for complete search history.

(56) References Cited

U.S. PATENT DOCUMENTS 4,466,426 A    8/1984 Blackman
4,636,217 A    1/1987 Ogilvie et al.
(Continued)

FOREIGN PATENT DOCUMENTS

WO    WO 2006/102485    9/2006
WO    WO 2006/105437 A2    10/2006
(Continued)

OTHER PUBLICATIONS

Bacfuse® Spinous Process Fusion Plate Surgical Technique, 2011, Pioneer Surgical, 12 pages.
(Continued)

*Primary Examiner* — Larry E Waggle, Jr.
(74) *Attorney, Agent, or Firm* — Foley & Lardner LLP

(57) ABSTRACT

An expandable implant includes a base member including a top surface, a first end, and a second end, and defining a central cavity positioned between the first end and the second end; an adjustable member including a top surface and at least one control channel, wherein the adjustable member is adjustably coupled to the base member and movable between a first, collapsed position, and a second, expanded position; a control shaft rotatable received by the base member, wherein rotation of the control shaft cause relative movement of the adjustable member relative to the base member; and at least one control member received on the control shaft and by the control channel, wherein rotation of the control shaft causes the control member to translate along the control shaft and along the control channel.

19 Claims, 20 Drawing Sheets

Related U.S. Application Data which is a continuation-in-part of application No. 13/802,110, filed on Mar. 13, 2013, now Pat. No. 9,034,041.

(52) U.S. Cl.
CPC .............. *A61F 2/442* (2013.01); *A61F 2/446* (2013.01); *A61F 2/447* (2013.01); *A61F 2/4455* (2013.01); *A61F 2002/3037* (2013.01); *A61F 2002/3055* (2013.01); *A61F 2002/30158* (2013.01); *A61F 2002/30163* (2013.01); *A61F 2002/30179* (2013.01); *A61F 2002/30428* (2013.01); *A61F 2002/30471* (2013.01); *A61F 2002/30482* (2013.01); *A61F 2002/30492* (2013.01); *A61F 2002/30507* (2013.01); *A61F 2002/30523* (2013.01); *A61F 2002/30537* (2013.01); *A61F 2002/30556* (2013.01); *A61F 2002/30579* (2013.01); *A61F 2002/30594* (2013.01); *A61F 2002/30784* (2013.01); *A61F 2002/30828* (2013.01); *A61F 2002/30841* (2013.01); *A61F 2002/30879* (2013.01); *A61F 2002/30904* (2013.01); *A61F 2002/4415* (2013.01); *A61F 2310/00017* (2013.01); *A61F 2310/00023* (2013.01)

(56) References Cited

U.S. PATENT DOCUMENTS

| | | |
|---|---|---|
| 4,863,476 A | 9/1989 | Shepperd |
| 5,390,683 A | 2/1995 | Pisharodi |
| 5,645,599 A | 7/1997 | Samani |
| 5,658,335 A | 8/1997 | Allen |
| 5,658,337 A | 8/1997 | Kohrs et al. |
| 5,836,948 A | 11/1998 | Zucherman et al. |
| 5,860,977 A | 1/1999 | Zucherman et al. |
| 5,876,404 A | 3/1999 | Zucherman et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,126,689 A | 10/2000 | Brett |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,375,682 B1 | 4/2002 | Fleischmann et al. |
| 6,409,766 B1 | 6/2002 | Brett |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,648,917 B2 | 11/2003 | Gerbec et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,773,460 B2 | 8/2004 | Jackson |
| 6,796,983 B1 | 9/2004 | Zucherman et al. |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,217,291 B2 | 5/2007 | Zucherman et al. |
| 7,621,950 B1 | 11/2009 | Globerman et al. |
| 7,695,513 B2 | 4/2010 | Zucherman et al. |
| 7,731,751 B2 | 6/2010 | Butler et al. |
| 7,879,098 B1 | 2/2011 | Simmons, Jr. |
| 8,016,861 B2 | 9/2011 | Mitchell et al. |
| 8,048,117 B2 | 11/2011 | Zucherman et al. |
| 8,105,382 B2 | 1/2012 | Olmos et al. |
| 8,231,656 B2 | 7/2012 | Lee et al. |
| 8,241,330 B2 | 8/2012 | Lamborne et al. |
| 8,303,663 B2 | 11/2012 | Jimenez et al. |
| 8,343,190 B1 | 1/2013 | Mueller et al. |
| 8,353,963 B2 | 1/2013 | Glerum |
| 8,382,801 B2 | 2/2013 | Lamborne et al. |
| 8,597,360 B2 | 12/2013 | McLuen et al. |
| 8,894,711 B2 | 11/2014 | Varela |
| 8,894,712 B2 | 11/2014 | Varela |
| 9,034,041 B2 | 5/2015 | Wolters et al. |
| 9,532,883 B2 | 1/2017 | McLuen et al. |
| 2002/0128716 A1 | 9/2002 | Cohen et al. |
| 2003/0040746 A1 | 2/2003 | Mitchell et al. |
| 2003/0236520 A1 | 12/2003 | Lim et al. |
| 2004/0153156 A1 | 8/2004 | Cohen et al. |
| 2004/0167625 A1 | 8/2004 | Beyar et al. |
| 2005/0033437 A1 | 2/2005 | Bao et al. |
| 2005/0070911 A1 | 3/2005 | Carrison et al. |
| 2005/0131536 A1 | 6/2005 | Eisermann et al. |
| 2005/0143827 A1 | 6/2005 | Globerman et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0036258 A1 | 2/2006 | Zucherman et al. |
| 2006/0084988 A1 | 4/2006 | Kim |
| 2006/0089718 A1 | 4/2006 | Zucherman et al. |
| 2006/0095136 A1 | 5/2006 | McLuen |
| 2006/0189999 A1 | 8/2006 | Zwirkoski |
| 2006/0241601 A1 | 10/2006 | Trautwein et al. |
| 2006/0264938 A1 | 11/2006 | Zucherman et al. |
| 2007/0142915 A1 | 6/2007 | Altarac et al. |
| 2008/0114456 A1 | 5/2008 | Dewey et al. |
| 2008/0140207 A1 | 6/2008 | Olmos et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0312741 A1 | 12/2008 | Lee et al. |
| 2009/0062915 A1 | 3/2009 | Kohm et al. |
| 2010/0179655 A1 | 7/2010 | Hansell et al. |
| 2010/0211176 A1 | 8/2010 | Greenhalgh |
| 2010/0241167 A1 | 9/2010 | Taber et al. |
| 2011/0022090 A1 | 1/2011 | Gordon et al. |
| 2011/0066186 A1 | 3/2011 | Boyer et al. |
| 2011/0144692 A1 | 6/2011 | Saladin et al. |
| 2011/0172709 A1 | 7/2011 | Lyons et al. |
| 2011/0184468 A1 | 7/2011 | Metcalf et al. |
| 2011/0224731 A1 | 9/2011 | Smisson et al. |
| 2011/0282453 A1 | 11/2011 | Greenhalgh et al. |
| 2011/0319997 A1 | 12/2011 | Glerum et al. |
| 2012/0016418 A1 | 1/2012 | Chin et al. |
| 2012/0059474 A1 | 3/2012 | Weiman |
| 2012/0109203 A1 | 5/2012 | Dryer et al. |
| 2012/0221051 A1 | 8/2012 | Robinson |
| 2012/0330422 A1 | 12/2012 | Weiman |
| 2013/0085572 A1 | 4/2013 | Glerum et al. |
| 2013/0103156 A1 | 4/2013 | Packer et al. |
| 2013/0158664 A1 | 6/2013 | Palmatier et al. |
| 2013/0158668 A1 | 6/2013 | Nichols et al. |
| 2013/0158669 A1* | 6/2013 | Sungarian ............... A61F 2/442 623/17.16 |
| 2013/0211526 A1* | 8/2013 | Alheidt .................. A61F 2/4611 623/17.16 |
| 2014/0148904 A1 | 5/2014 | Robinson |
| 2014/0236296 A1* | 8/2014 | Wagner .................. A61F 2/447 623/17.15 |
| 2014/0277473 A1 | 9/2014 | Perrow |
| 2014/0277500 A1 | 9/2014 | Logan et al. |
| 2015/0100128 A1 | 4/2015 | Glerum et al. |
| 2015/0173917 A1 | 6/2015 | Radcliffe et al. |
| 2016/0242927 A1 | 8/2016 | Seifert et al. |
| 2017/0056197 A1 | 3/2017 | Weiman et al. |

FOREIGN PATENT DOCUMENTS

| | | |
|---|---|---|
| WO | WO 2009/124269 | 10/2009 |
| WO | WO 2016/077610 A1 | 5/2016 |
| WO | WO 2016/127139 A1 | 8/2016 |

(56) References Cited

FOREIGN PATENT DOCUMENTS

WO    WO 2017/027873 A1    2/2017
WO    WO 2017/066463 A1    4/2017

OTHER PUBLICATIONS

Extended European Search Report for European Application No. 14159101.6, dated Jun. 18, 2014, 6 pages.
Extended European Search Report for European Application No. 16169890.7, dated Oct. 21, 2016, 7 pages.
International Preliminary Report on Patentability for Application No. PCT/US06/12060, dated Jul. 18, 2007, 3 pages.
International Search Report and Written Opinion for International Application No. PCT/US2012/057324, dated Dec. 20, 2012, 10 pages.
International Search Report for Application No. PCT/US06/12060, dated Apr. 5, 2007, 1 page.
Written Opinion of the International Searching Authority for Application No. PCT/US06/12060, dated Apr. 5, 2007, 3 pages.
Search Report for International Application No. PCT/US2018/029120, dated Jun. 28, 2018, 17 pages.
Search Report for International Application No. PCT/US2018/029149, dated Jun. 25, 2018, 13 pages.
Search Report for International Application No. PCT/US2018/041306, dated Sep. 28, 2018, 12 pages.

\* cited by examiner

EXPANDABLE IMPLANT ASSEMBLY

CROSS-REFERENCE TO RELATED PATENT APPLICATIONS

This application is a continuation in part of application Ser. No. 14/714,821, filed May 18, 2015, which is a continuation in part of application Ser. No. 13/802,110, filed Mar. 13, 2013, both of which are incorporated herein by reference in their entireties.

BACKGROUND

The present disclosure relates to expandable implants and devices, including spinal interbody and intravertebral body devices, and vertebral interbody and intravertebral devices that are expandable after spinal placement thereof.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

A problem with most spinal interbody and intravertebral devices is that they are static in size. This poses various problems with their use and/or implantation. Particularly, static sized spinal devices are fairly large in order to properly bridge the gap between adjacent vertebrae. This large size does not lend itself to microsurgery, arthroscopic surgery or the like.

Devices are now being made that are expandable. Expandable interbody devices allow the device to be initially smaller than traditional non-expandable (static) interbody devices such that expandable interbody devices may be more easily inserted or implanted into the vertebral space. Moreover, expandable devices allow the surgeon to set the amount of expansion necessary for the particular patient rather than the static device dictating the spacing.

SUMMARY

One embodiment relates to an expandable implant, including a base member including a top surface, a first end, and a second end, and defining a central cavity positioned between the first end and the second end; an adjustable member including a top surface and at least one control channel, wherein the adjustable member is adjustably coupled to the base member and movable between a first, collapsed position, and a second, expanded position; a control shaft rotatably received by the base member, wherein rotation of the control shaft cause relative movement of the adjustable member relative to the base member; and at least one control member received on the control shaft and by the control channel, wherein rotation of the control shaft causes the control member to translate along the control shaft and along the control channel.

Another embodiment relates to an expandable implant, including a base member including a top surface, a first end, and a second end, and defining a central cavity positioned between the first end and the second end; an adjustable member including a top surface, a first control channel, and a second control channel; a control shaft rotatably received by the base member, wherein the control shaft defines a first acute angle with the first control channel and a second acute angle with the second control channel, and wherein rotation of the control shaft causes relative movement of the adjustable member relative to the base member; a first control member received on the control shaft and by the first control channel such that rotation of the control shaft causes translation of the first control member along the control shaft and along the first control channel; and a second control member received on the control shaft and by the second control channel such that rotation of the control shaft causes translation of the second control member along the control shaft and along the second control channel.

Another embodiment relates to an expandable implant, including a base member; an adjustable member movably coupled to the base member and defining a first control channel and a second control channel; a control shaft translationally fixed and rotatable movable relative to the base member, wherein rotation of the control shaft causes relative movement of the adjustable member relative to the base member, wherein the control shaft defines a first intersection angle with the first control channel and a second different intersection angle with the second control channel; a first control member received on the control shaft and in the first control channel such that rotation of the control shaft causes translation of the first control member along the control shaft and within the first control channel; and a second control member received on the control shaft and within the second control channel such that rotation of the control shaft causes translation of the first control member along the control shaft and within the first control channel.

BRIEF DESCRIPTION

The foregoing and other features of the present invention will become more apparent to one skilled in the art upon also reading the following description of embodiments with reference to the accompanying drawings.

FIG. 28 is a perspective view of the implant of FIG. 27 in an expanded position according to one embodiment.

Figure 1:
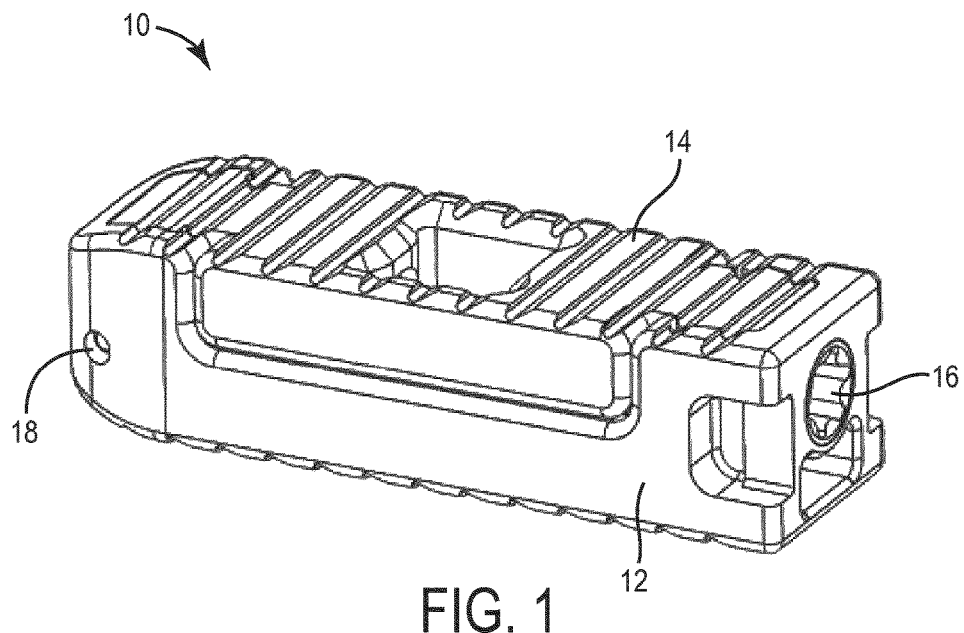
FIG. 1 is perspective view of an expandable implant in a collapsed position according to one embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

The present disclosure relates to expandable and/or dynamic implants, including, but not limited to, interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (expandable and/or expandable and retractable) interbody/intravertebral body devices that are usable in a spinal column or other areas of a human.

Various embodiments disclosed herein are directed to expandable implants that are implantable between adjacent bodies of bone. For example, the implant may implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

Referring now to FIGS. 1-9C, an expandable implant 10 is shown according to an exemplary embodiment. Implant 10 is usable, for example, between and/or within vertebral bodies of the spine, and may share many of the features of the other inter/intra-body implants discussed elsewhere herein. It should be understood that implant 10 may in some embodiments be usable in other portions of the body in addition to the spine, and all such applications are to be understood to be within the scope of the present disclosure.

Figure 2:
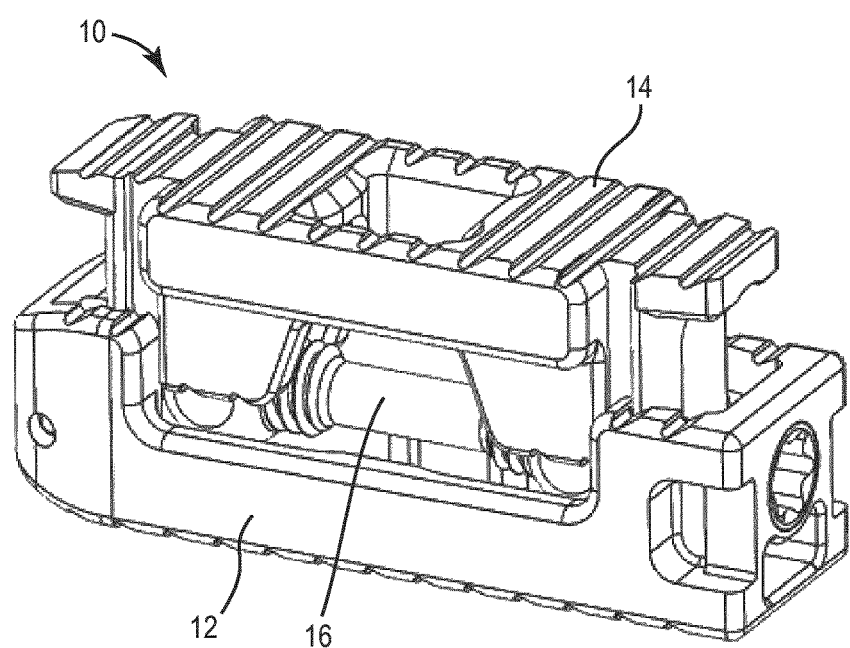
FIG. 2 is a perspective view of the implant of FIG. 1 in an expanded position according to one embodiment.
Figure 3:
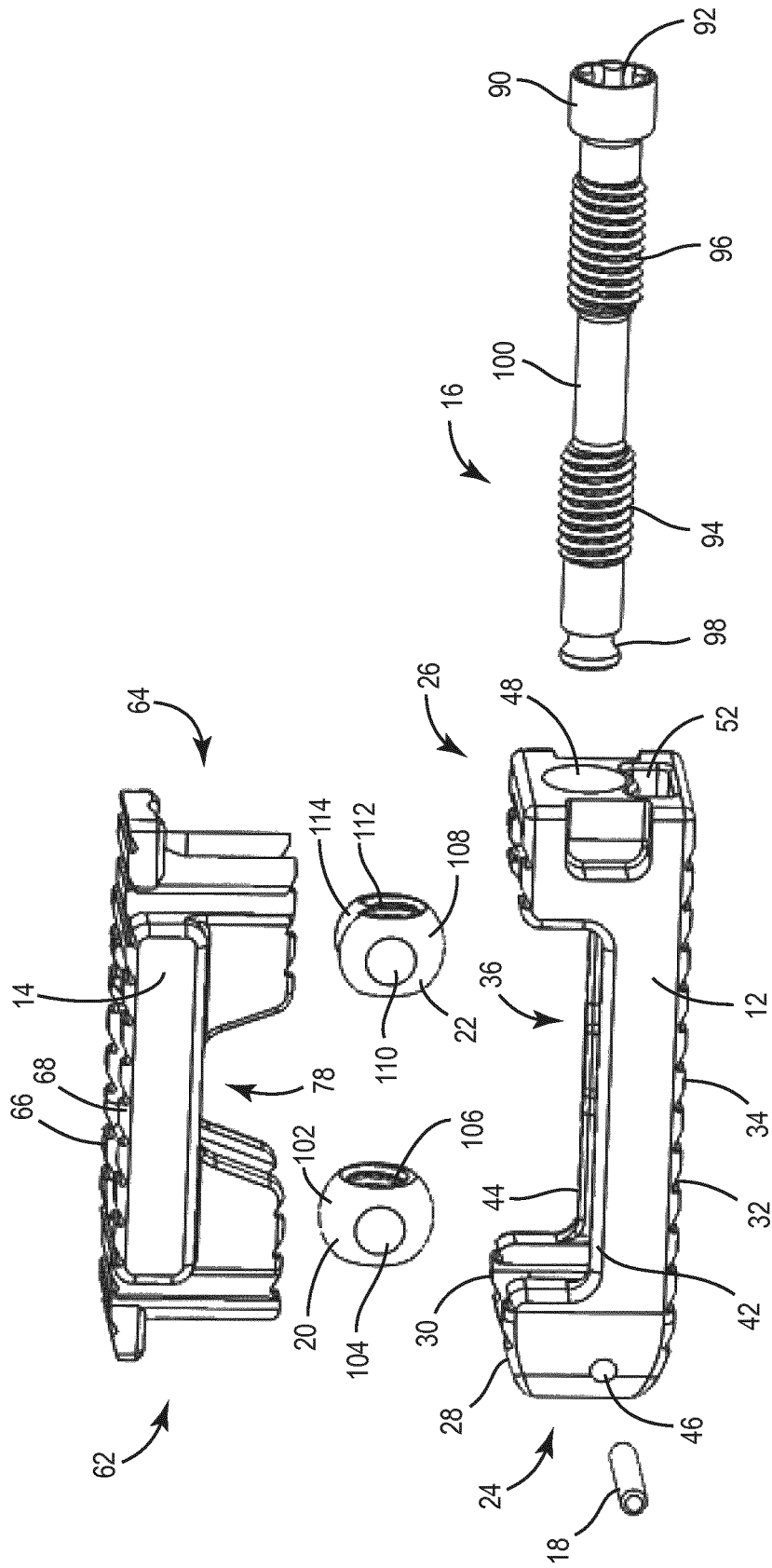
FIG. 3 is an exploded view of the implant of FIG. 1 according to one embodiment.

According to an exemplary embodiment, implant 10 includes a base member 12 and an adjustable member 14 adjustably coupled to the base member 12. A control shaft 16 is received by the base member 12 and is retained by a retention pin 18 passing through a portion of the base member 12. A first control member 20 and a second control member 22 are received on the control shaft 16 and are movable along the control shaft 16 to adjust a position of the adjustable member 14 between a collapsed position, as shown in FIG. 1, and an expanded position, as shown in FIG. 2.

Figure 6:
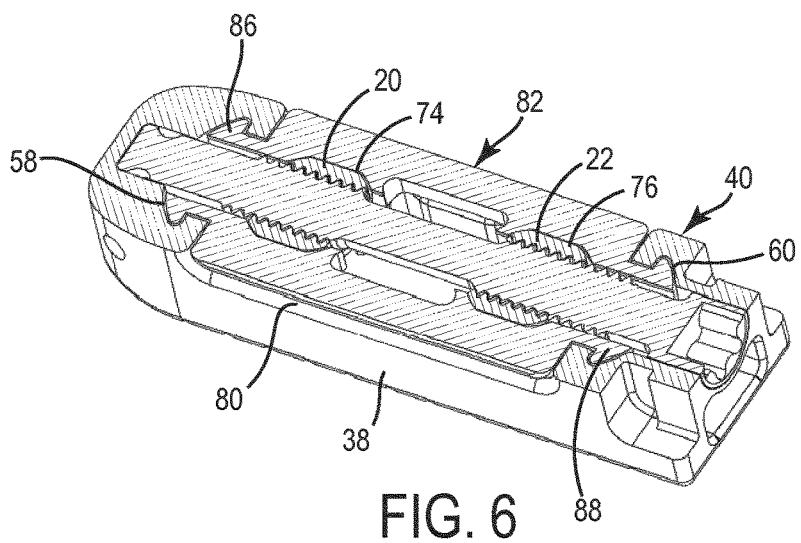
FIG. 6 is a top cross-sectional view of the implant of FIG. 1 according to one embodiment.
Figure 7:
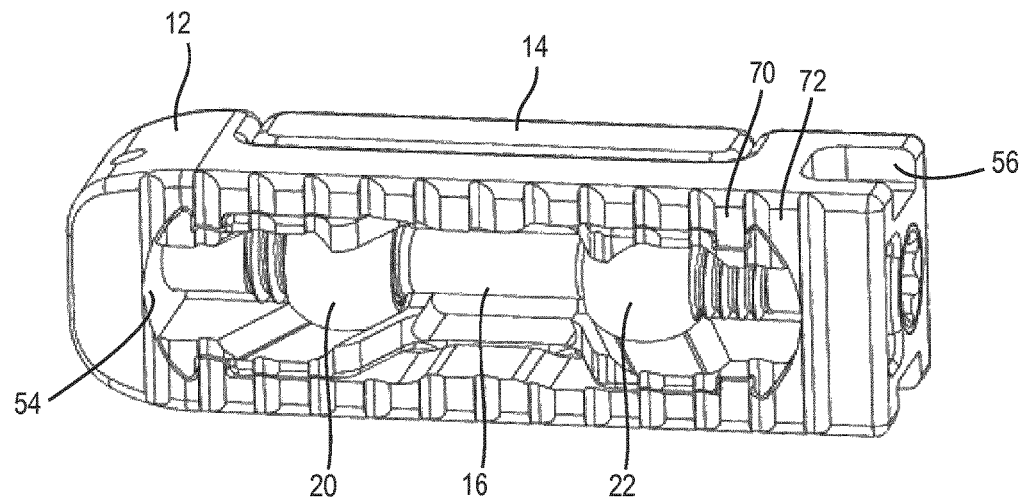
FIG. 7 is a bottom perspective view of the implant of FIG. 1 in a collapsed position according to one embodiment.
Figure 8:
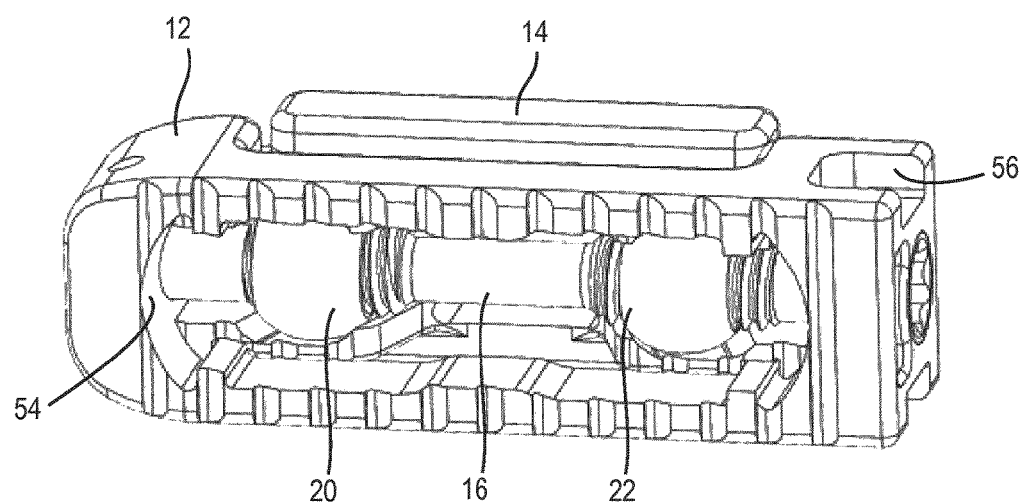
FIG. 8 is a bottom perspective view of the implant of FIG. 1 in an expanded position according to one embodiment.

In one embodiment, the base member 12 includes a front or first end 24, a rear or second end 26, and a central cavity 36 disposed between the first end 24 and the second end 26. The base member 12 further includes a top surface 28 having ridges or projections 30 formed by corresponding grooves, a bottom surface 32 opposite the top surface 28 and having ridges or projections 34 formed by corresponding grooves, a first side 38, and a second side 40. The projections 30, 34 are configured to engage adjacent portions of bone. The first side 38 defines a first side recess 42, and the second side 40 defines a second side recess 44. A pin aperture 46 extends through one or both of first side 38 and second side 40 and is configured to receive the retention pin 18 (e.g., in a press fit or other manner). The second end 26 of the base member 12 includes a control bore 48 configured to receive a first portion of the control shaft 16. The first end 24 of the base member 12 includes a control counterbore 50 (see FIG. 4) configured to receive a second portion of the control shaft 16. As shown in FIG. 6, in some embodiments, the first end 24 of the base member 12 further includes a dovetail recess 58, and the second end 26 of the base member 12 further includes a dovetail recess 60.

In one embodiment, the adjustable member 14 includes a front or first end 62, a rear or second end 64, and a central recess or cavity 78 positioned between the first end 62 and the second end 64. A top cavity 84 (see FIG. 5) in the adjustable member 14 extends to the central cavity 78. The adjustable member 14 further includes a top surface 66 having ridges or projections 68 formed by corresponding grooves, a bottom surface 70 including ridges or projections 72 (see FIG. 8) formed by corresponding grooves, a first side portion 80, and a second side portion 82. In some embodiments, the first and second side portions 80, 82 have shapes generally corresponding to the shapes of the first and second side recesses 42, 44 of base member 12. In other embodiments, the first and second side portions 80, 82 have shapes differing from the shapes of the first and second side recesses 42, 44 of the base member 12. The first end 62 of the adjustable member 14 further includes a dovetail projection 86, and the second end 64 of the adjustable member 14 further includes a dovetail projection 88.

Figure 4:
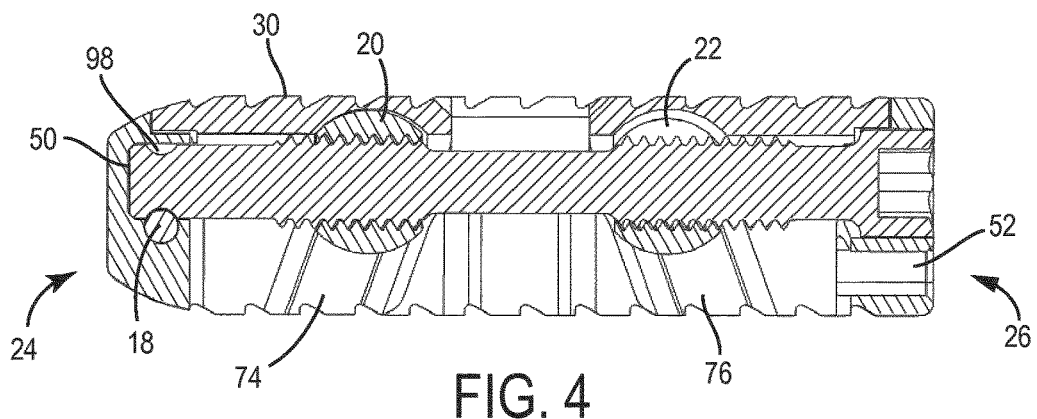
FIG. 4 is a side cross-sectional view of the implant of FIG. 1 in a collapsed position according to one embodiment.
Figure 5:
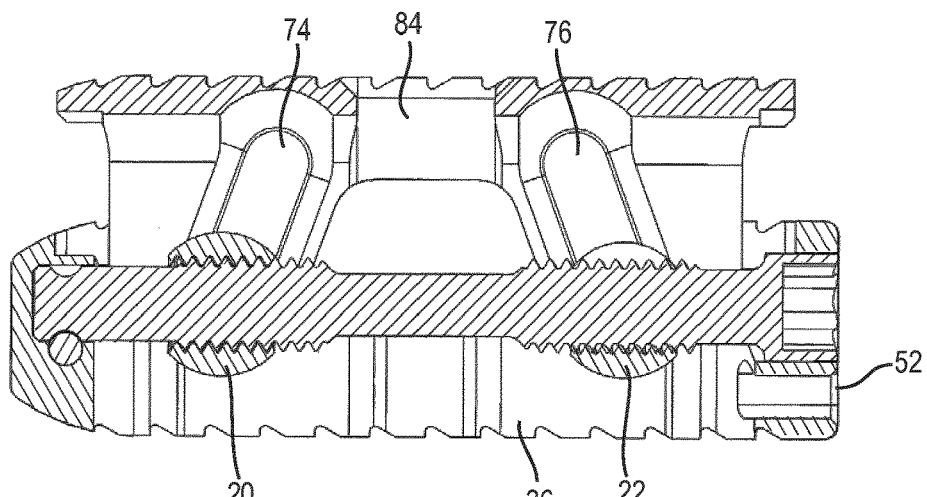
FIG. 5 is a side cross-sectional view of the implant of FIG. 1 in an expanded position according to one embodiment.

Referring to FIGS. 4-6, in one embodiment, the adjustable member 14 includes one or more control channels, such as a first control channel 74 and a second control channel 76. The first control channel 74 receives the first control member 20, and the second control channel 76 receives the second control member 22. In some embodiments, the control members 20, 22 are received in the control channels 74, 76 in a sliding manner such that the control members 20, 22 are able to translate within the control channels 74, 76. In further embodiments, each control channel has a shape such that the control channel surrounds the control member and at least partially corresponds in shape to the control member.

Referring back to FIG. 3, the control shaft 16 includes a head portion 90, a tool port 92 disposed within the head portion 90, and a retention groove 98 located at an end opposite the head portion 90. In some embodiments, the control shaft 16 further includes a first control thread 94 and a second control thread 96. A non-threaded portion 100 may be located between the first control thread 94 and the second control thread 96.

The first control member 20 includes a body 102, one or more flat portions 104, and a first internal thread 106. The second control member 22 includes a body 108, one or more flat portions 110, and a second internal thread 112. In some embodiments, the second control member 22 further includes a slotted portion 114 configured to enable passing the second control member 22 over a portion (e.g., non-threaded portion 100) of the control shaft 16. The first control member 20 and the second control member 22 move or translate both along the control shaft 16 and within or on the first control channel 74 and the second control channel 76.

Referring back to FIGS. 1 and 2, implant 10 is movable between a first, collapsed position, as shown in FIG. 1, to a second, expanded position, shown in FIG. 2. In the first position, the adjustable member 14 is received within the central cavity 36 of the base member 12. The dovetail projections 86, 88 on the adjustable member 14 are received within the dovetail recesses 58, 60 in the base member 12 (see FIG. 6). In some embodiments, the projections and recesses have a relatively close fit to enable proper alignment between the adjustable member 14 and the base member 12, while in other embodiments, the projections and recesses have a relatively loose fit to enable a desired angular offset between the adjustable member 14 and the base member 12.

Referring to FIGS. 3-6, the control shaft 16 is received by the base member 12 such that the retention groove 98 is positioned with the first end 24 of the base member 12 and the head portion 90 is positioned within the second end 26 of the base member 12. In one embodiment, the control shaft 16 is rotatable within the base member 12, and the retention pin 18 extends through the first end 24 and into the retention groove 98 of the control shaft 16 to enable rotation of the control shaft 16 while inhibiting translation of the control shaft 16 relative to the base member 12. The first control member 20 is received on the first control thread 94 of the control shaft 16, and the second control member 22 is received on the second control thread 96 of the control shaft 16. To facilitate assembly of implant 10, in some embodiments, the slot 114 enables passage of the second control member 22 over the non-threaded portion 100 of the control shaft 16 and subsequent threading of the second control member 22 onto the second control thread 96.

In one embodiment, the first control thread 94 and the second control thread 96 are threaded in opposite manners (e.g., left-handed and right-handed), such that upon rotation of the control shaft 16, the control members 20, 22 move in opposite directions along the control shaft 16. For example, the control shaft may be configured that rotation of the control shaft 16 in a first direction (e.g., clockwise) causes the first and second control members 20, 22 to move toward each other, and rotation of the control shaft 16 in a second direction (e.g., counter-clockwise) causes the first and second control member 20, 22 to move away from each other.

As shown in FIGS. 4 and 5, as the control members 20, 22 move along the control shaft 16, the control members 20, 22 further move within the control channels 74, 76, thereby causing relative movement of the adjustable member 14 and the base member 12. For example, FIGS. 4 and 5 show the control members 20, 22 moving away from each other along the control shaft 16. As the control members 20, 22 translate along the control shaft 16, the adjustable member 14 is moved upward or downward due to the angled shape of the first and second control channels 74, 76. The rate of movement of the control members 20, 22, and therefore the adjustable member 14, can be adjusted by modifying the slope of the control channels 74, 76 relative to the control shaft 16.

Figure 9A:
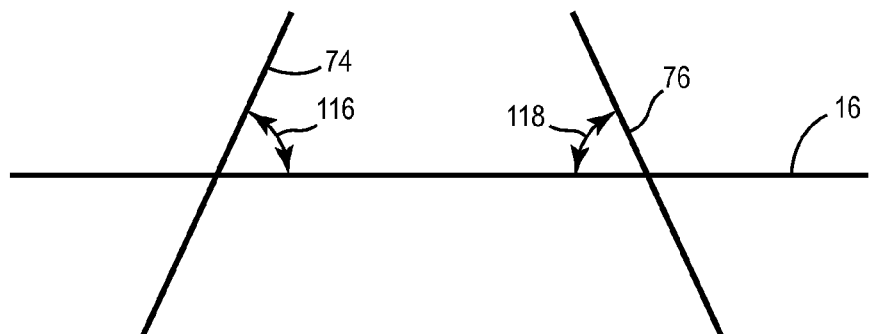
FIG. 9A is a schematic view of a control scheme usable with the implant of FIG. 1 according to one embodiment.
Figure 9B:
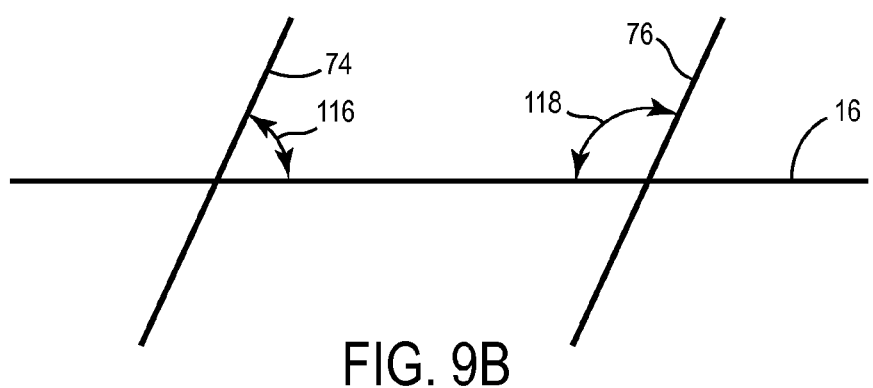
FIG. 9B is a schematic view of a control scheme usable with the implant of FIG. 1 according to another embodiment.
Figure 9C:
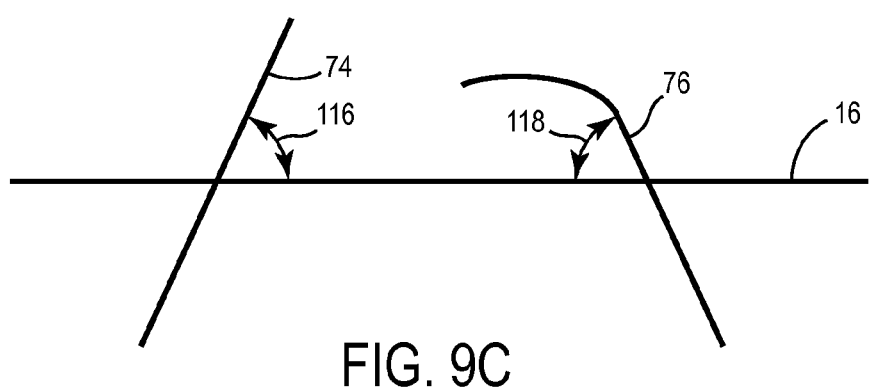
FIG. 9C is a schematic view of a control scheme usable with the implant of FIG. 1 according to another embodiment.

For example, referring to FIGS. 9A-9C, schematic representations of the control shaft 16, the first control channel 74, and the second control channel 76 are shown according to various alternative embodiments. The first control channel 74 extends at a first angle 116 relative to the control shaft 16, and the second control channel 76 extends at a second angle 118 relative to the control shaft 16. The first and second angles 116, 118 define the rate at which first control member 20 and second control member 22 cause corresponding movement (e.g., expansion) of the first and second ends 62, 64 of the adjustable member 14 relative to the base member 12. As shown in FIG. 9A, in some embodiments, the first angle 116 and second angle 118 are approximately the same, and the control channels 74, 76 define linear paths, such that the rates of movement of the first and second ends 62, 64 of the adjustable member 14 are substantially the same and constant (assuming a constant rate of rotation of the control shaft 16). As shown in FIG. 9B, in some embodiments, rather than being angled toward each other in an upward direction, the first and second control channels 74, 76 may extend in a parallel manner or be configured to extend upward at angles in the same general direction. In yet further embodiments, one or both of the control channels 74, 76 may define a non-linear channel. For example, as shown in FIG. 9C, the second control channel 76 defines a curved path, thereby providing a changing rate of movement of the second end 64 of adjustable member 14. In further alternative embodiments, angles 116, 118 may differ from each other to provide different amounts of movement and to suit a particular application.

Providing differing configurations for the first control channel 74 and the second control channel 76 enables customization of the characteristics of the implant 10 in the second, expanded position. For example, the control channels 74, 76 may be configured such that in a fully expanded position of implant 10, one of the first end 62 and the second end 64 of the adjustable member 14 is expanded to a greater degree than the opposing end. An example of such a configuration is reflected in FIG. 9C, and shown in greater detail with the embodiment of FIGS. 27-34. Other configurations of the first and second control channels 74, 76 are possible according to various alternative embodiments.

In use, implant 10 is positioned within a desired space (e.g., between adjacent portions of bone) while in the first, collapsed position, as shown in FIG. 1. To position implant 10, an appropriate tool may be used to engage tool recesses 56 and manipulate implant 10 into a desired position. Once in a desired position, a subsequent tool may be utilized to engage tool port 92 and rotate control shaft 16 to move adjustable member 14 to a desired degree of expansion. It should be noted that based on a particular application, the adjustable member 14 may be utilized in a fully collapsed position, a fully expanded position, or any intermediate position therebetween. Once implant 10 is properly positioned and expanded to a desired height, bone graft material may be delivered by way of, for example, access aperture 52 and placed into central cavity 36. The various apertures in and through the base member 12 and adjustable member 14 may in some embodiments facilitate the growth of bone material in and around implant 10 to further stabilize the device.

It should be noted that implant 10 may share various features with the other implants described herein, and be made of the same, similar, or different materials. For example, various components of implant 10 may be made of metal, plastic, composites, or other suitable bio-compatible materials. Further, implant 10 may be usable in connection with the spine or other parts of the body.

Referring now to FIGS. 10-15, an expandable implant 210 is shown according to an exemplary embodiment. Implant 210 may share many of the features of the other inter/intrabody implants discussed elsewhere herein. All such combinations of features are to be understood to be within the scope of the present disclosure. Implant 110 is generally similar to implant 10 in structure and function except that, while implant 10 expands to vary an implant height, implant 210 expands to vary an implant width.

Figure 10:
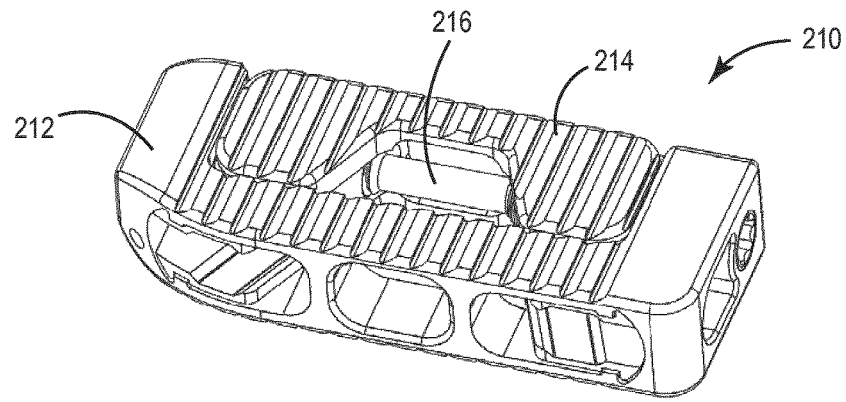
FIG. 10 is a perspective view of an expandable implant in a collapsed position according to another embodiment.
Figure 11:
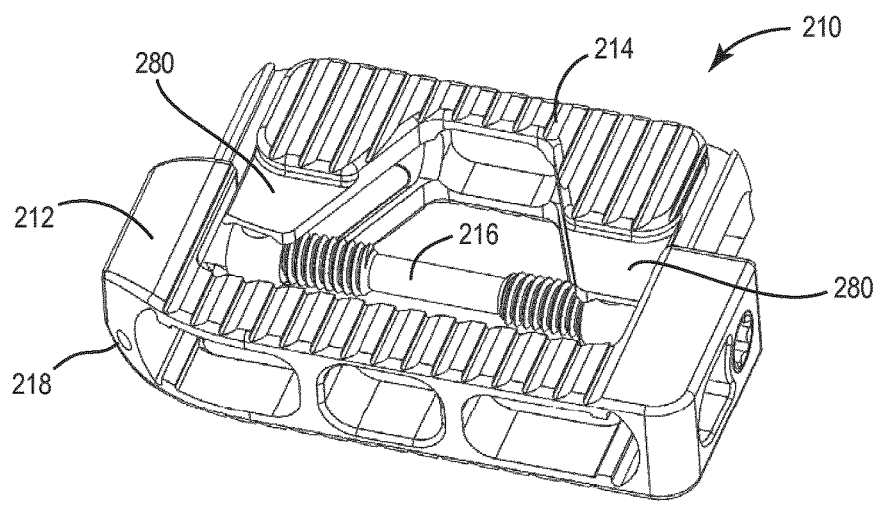
FIG. 11 is a perspective view of the implant of FIG. 10 in an expanded position according to one embodiment.
Figure 12:
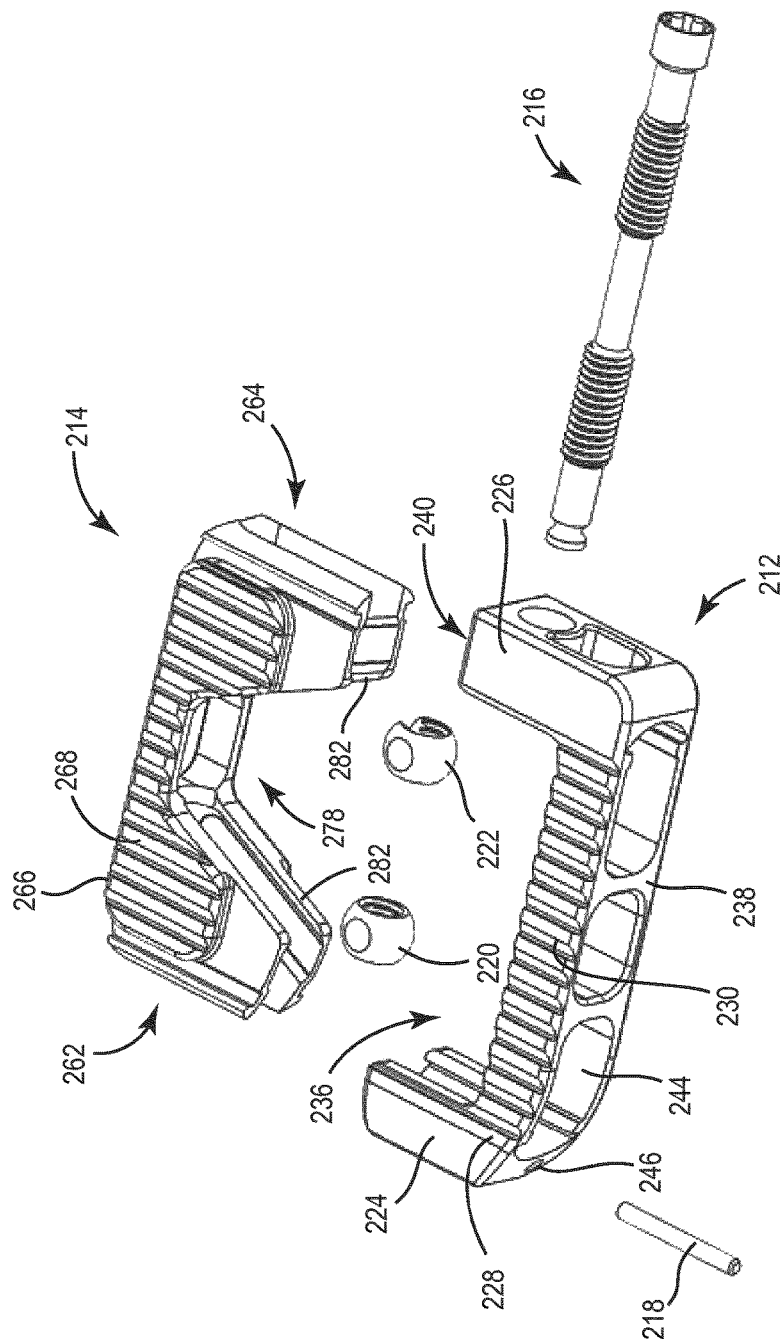
FIG. 12 is an exploded view of the implant of FIG. 10 according to one embodiment.

Implant 210 includes a base member 212 and an adjustable member 214 adjustably coupled to the base member 212. A control shaft 216 is received by the base member 212 and is retained by a retention pin 218 passing through a portion of the base member 212. A first control member 220 and a second control member 222 are received on the control shaft 216 and are movable along the control shaft 216 to adjust a position of the adjustable member 214 between a collapsed position, as shown in FIG. 10, and an expanded position, as shown in FIG. 11.

In one embodiment, the base member 212 includes a front or first end 224, a rear or second end 226, and a central cavity 236 disposed between the first end 224 and the second end 226. The base member 212 further includes a top surface 228 having ridges or projections 230 formed by corresponding grooves, a bottom surface 232 opposite the top surface 228 and having ridges or projections 234 formed by corresponding grooves, a first side 238, and a second side 240. The projections 230, 234 are configured to engage adjacent portions of bone. The first side 238 defines a plurality of recesses 244. A pin aperture 246 extends through one or both of the first side 238 and the second side 240 and is configured to receive the retention pin 218 (e.g., in a press fit or other manner). The second end 226 of the base member 212 includes a control bore 248 configured to receive a first portion of the control shaft 216. The first end 224 of the base member 212 includes a control counterbore 250 configured to receive a second portion of the control shaft 216. In some embodiments, the first end 224 of the base member 212 further includes a dovetail recess 258, and the second end 226 of the base member 212 further includes a dovetail recess 260.

In one embodiment, the adjustable member 214 includes a front or first end 262, a rear or second end 264, and a central recess or cavity 278 positioned between the first end 262 and the second end 264. A side cavity 284 in the adjustable member 214 extends to the central cavity 278. The adjustable member 214 further includes a top surface 266 having ridges or projections 268 formed by corresponding grooves, a bottom surface 270 including ridges or projections 272 formed by corresponding grooves, a pair of top portions 280, and a pair of bottom portions 282. In some embodiments, top and bottom portions 280, 282 are configured to slide underneath or within the top and bottom portions of base member 212 when implant 210 is in the first, collapsed position. The first end 262 of the adjustable member 214 further includes a dovetail projection 286, and the second end 264 of the adjustable member 214 further includes a dovetail projection 288.

Figure 13:
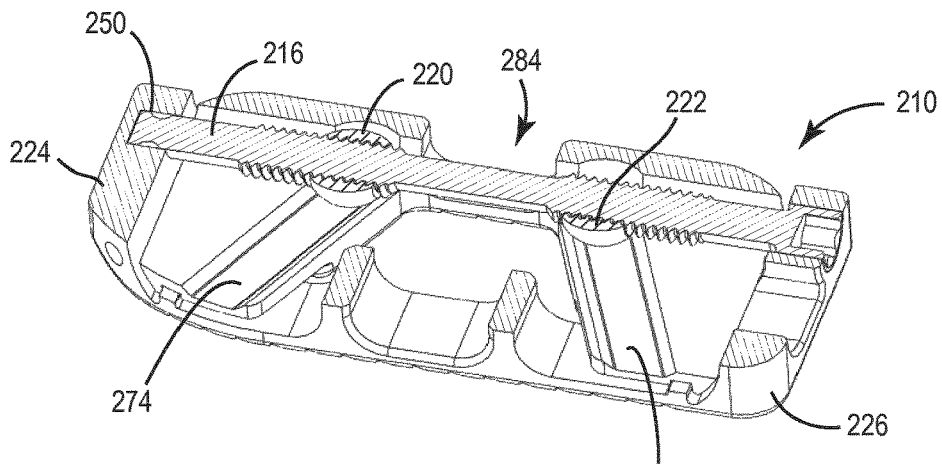
FIG. 13 is a side perspective cross-sectional view of the implant of FIG. 10 in a collapsed position according to one embodiment.
Figure 14:
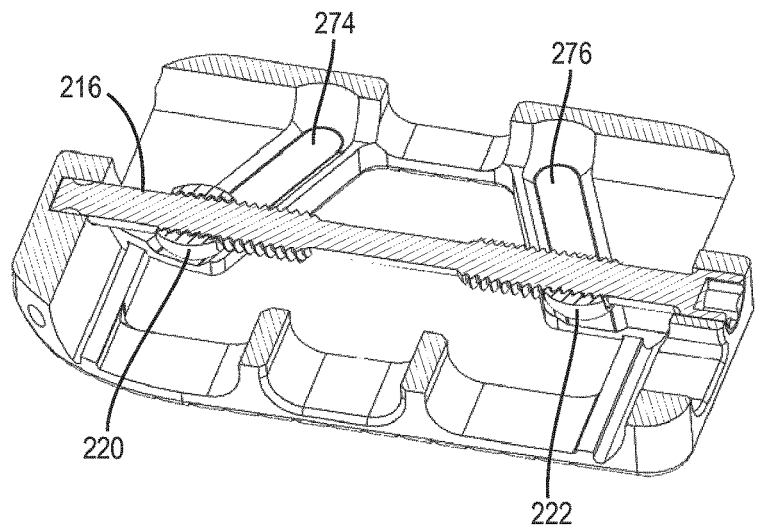
FIG. 14 is a side perspective cross-sectional view of the implant of FIG. 10 in an expanded position according to one embodiment.
Figure 15:
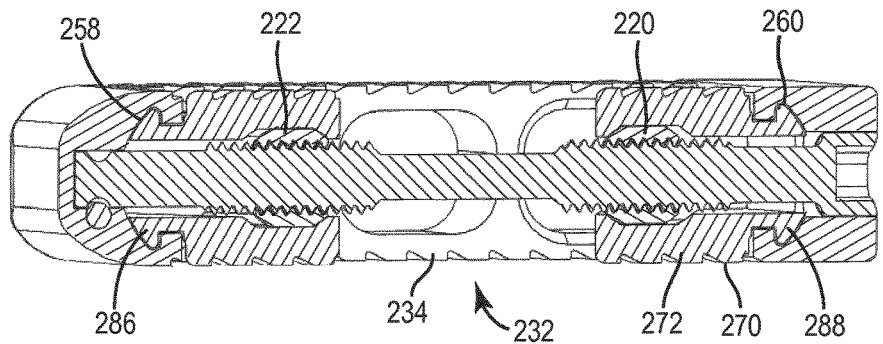
FIG. 15 is a top cross-sectional view of the implant of FIG. 1 according to one embodiment.

Referring to FIGS. 13-14, in one embodiment, the adjustable member 214 includes one or more control channels, such as a first control channel 274 and a second control channel 276. The first control channel 274 receives the first control member 220, and the second control channel 276 receives the second control member 222. In some embodiments, the control members 220, 222 are received in or on the control channels 274, 276 in a sliding manner such that the control members 220, 222 are able to translate within the control channels 274, 276. In further embodiments, each control channel has a shape such that the control channel surrounds the control member and at least partially corresponds in shape to the control member.

Implant 210 is adjustable in a similar manner to implant 10. However, while adjustment of implant 10 causes a change in height of the implant 10, adjustment of the implant 210 causes a change in width of the implant 210 (while maintaining a constant height). As such, while during adjustment of the implant 10, the top surface 66 of the adjustable member 14 may be offset from the top surface 28 of the base member 12, during adjustment of implant 210, the top surface 266 of the adjustable member 214 stays generally aligned with the top surface 228 of the base member 212. As such, the implant 210 may be used to provide, for example, a more stable implant by increasing the footprint of the implant and engagement areas with adjacent portions of bone. The implantation of the implant 210 is otherwise similar to that of the implant 10.

It should be noted that the implant 210 may share various features with the other implants described herein, and be made of the same, similar, or different materials. For example, various components of implant 210 may be made of metal, plastic, composites, or other suitable bio-compatible materials. Further, implant 210 may be usable in connection with the spine or other parts of the body.

Figure 16:
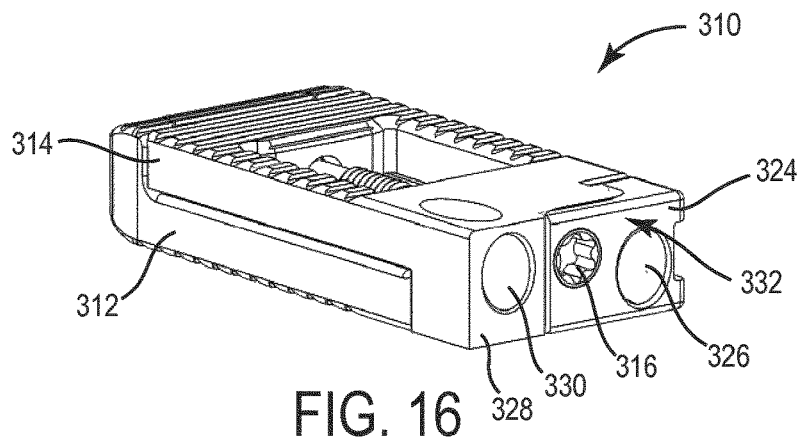
FIG. 16 is a perspective view of an expandable implant in a collapsed position according to another embodiment.
Figure 17:
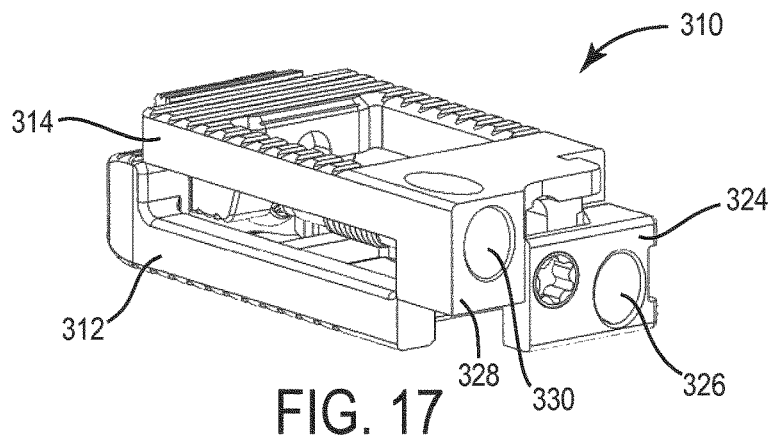
FIG. 17 is a perspective view of the implant of FIG. 16 in an expanded position according to one embodiment.
Figure 18:
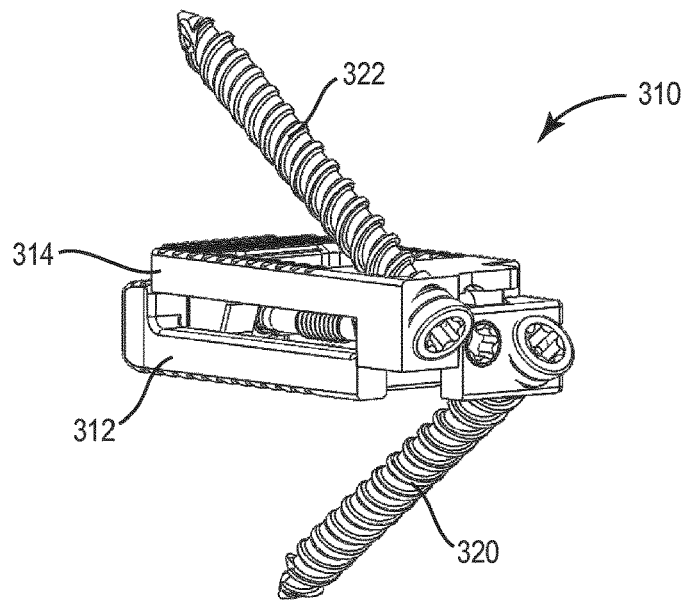
FIG. 18 is a perspective view of bone screws usable with the implant of FIG. 16 according to one embodiment.

Referring now to FIGS. 16-18, in some embodiments, one or both of a base member or an adjustable member of an implant may be configured to receive a bone screw to further secure the implant to adjacent portions of bone. For example, as shown in FIGS. 16-18, an implant 310 includes a base member 312 and an adjustable member 314 adjustably coupled to the base member 312. A control shaft 316 is received by the base member 312 and is retained by a retention pin passing through a portion of the base member 312. A first control member and a second control member are received on the control shaft 316 and are movable along the control shaft 316 to adjust a position of the adjustable member 314 between a collapsed position, as shown in FIG. 16, and an expanded position, as shown in FIG. 17. Bone screws 320, 322 extend through base member 312 and adjustable member 314.

Implant 310 may share any combination of the features disclosed herein with respect to the other implants, and all such combinations of features are to be understood to be within the scope of the present disclosure. In one embodiment, the implant 310 is generally rectangular in shape when in a first, collapsed position. As shown in FIG. 17, in some embodiments, the base member 312 includes a first bone screw support portion 324 having a first bone screw bore 326 configured to receive bone screw 320. Similarly, adjustable member 314 includes a second bone screw support portion 328 having a second bone screw bore 330 configured to receive bone screw 322. The first bone screw support portion 324 and the second bone screw support portion 328 collectively form a proximal face 332 for implant 310. As shown in FIG. 16, the first bone screw bore 326, the second bone screw bore 330, and the control shaft 316 are accessible by way of the proximal face 332 of the implant 310.

It should be noted that the implant 310 may share various features with the other implants described herein, and be made of the same, similar, or different materials. For example, various components of the implant 310 may be made of metal, plastic, composites, or other suitable bio-compatible materials. Further, the implant 310 may be usable in connection with the spine or other parts of the body.

Referring now to FIGS. 19-26, an expandable implant 410 is shown according to an exemplary embodiment. The implant 410 is usable, for example, between and/or within vertebral bodies of the spine, and may share any or all of the features of the other inter/intra-body implants discussed elsewhere herein. All such combinations of features are to be understood to be within the scope of the present disclosure. It should be understood that the implant 410 may in some embodiments be usable in other portions of the body in addition to the spine, and all such applications are to be understood to be within the scope of the present disclosure. The implant 410 is substantially similar to the implant 10 in structure and function except as discussed herein with respect to the control members and corresponding control rails.

Figure 19:
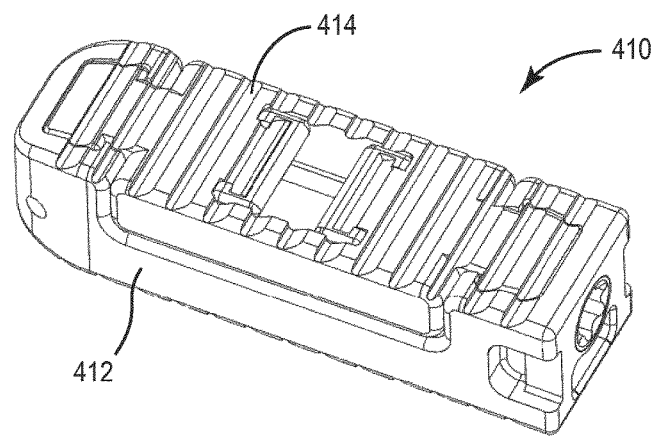
FIG. 19 is a perspective view of an expandable implant in a collapsed position according to another embodiment.
Figure 20:
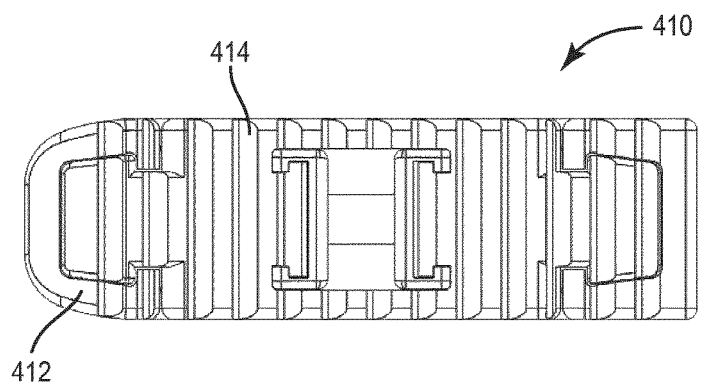
FIG. 20 is a top view of the implant of FIG. 19 according to one embodiment.
Figure 21:
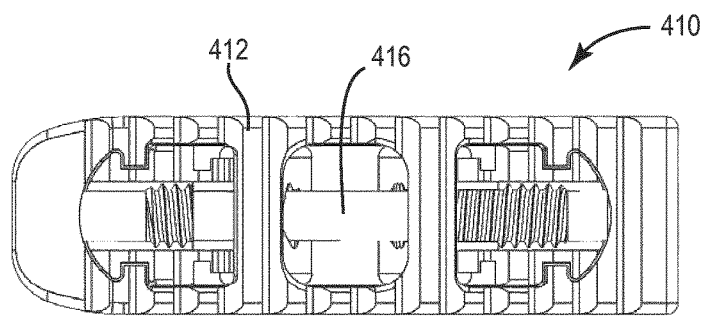
FIG. 21 is a bottom view of the implant of FIG. 19 according to one embodiment.
Figure 22:
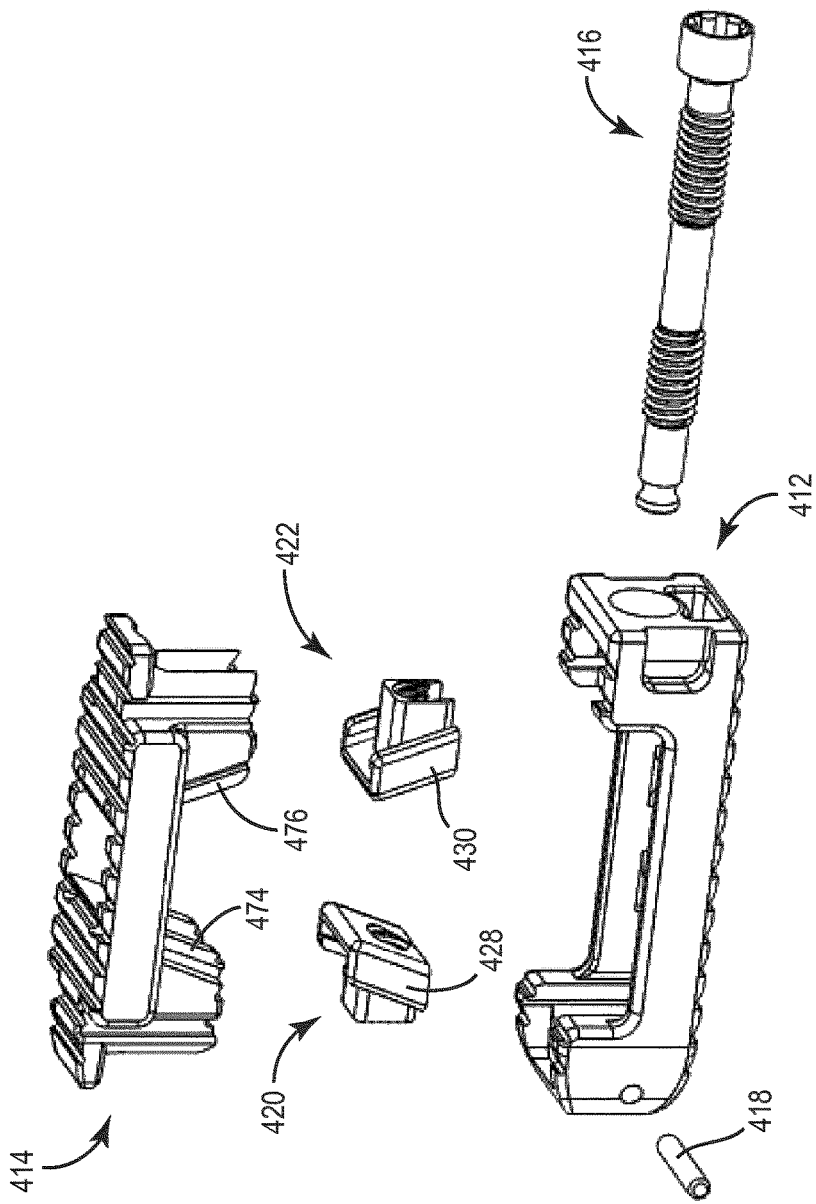
FIG. 22 is an exploded view of the implant of FIG. 19 according to one embodiment.

According to an exemplary embodiment, the implant 410 includes a base member 412 and an adjustable member 414 adjustably coupled to the base member 412. A control shaft 416 is received by the base member 412 and is retained by a retention pin 418 passing through a portion of the base member 412. A first control member 420 and a second control member 422 are received on the control shaft 416 and are movable along the control shaft 416 to adjust a position of the adjustable member 414 between a collapsed position, as shown in FIG. 19, and an expanded position, as shown in FIG. 23.

Referring to FIGS. 22-26, in one embodiment, the adjustable member 414 includes one or more control rails, such as a first control rail 474 and a second control rail 476. First control rail 474 receives first control member 420, and second control rail 476 receives second control member 422. In some embodiments, control members 420, 422 are received on control rails 474, 476 in a sliding manner such that the control members 420, 422 are able to translate on the control rails 474, 476. For example, the control rails 474, 476 may define control channels on or in which the control members 420, 422 are received. In further embodiments, each control rail has a shape such that the control member surrounds all or a portion of the control rail and at least partially corresponds in shape to the control rail.

The first control member 420 includes control arms 428 configured to engage the first control rail 474. The second control member 422 includes control arms 430 configured to engage the second control rail 476. The first control member 420 and the second control member 422 move or translate both along the control shaft 416 and along the first control rail 474 and the second control rail 476. In some embodiments, each control arm is substantially U-shaped and configured to wrap around an end portion of the corresponding control rail. In other embodiments, other shapes and/or configurations of control rails and control arms or other components may be utilized.

Figure 23:
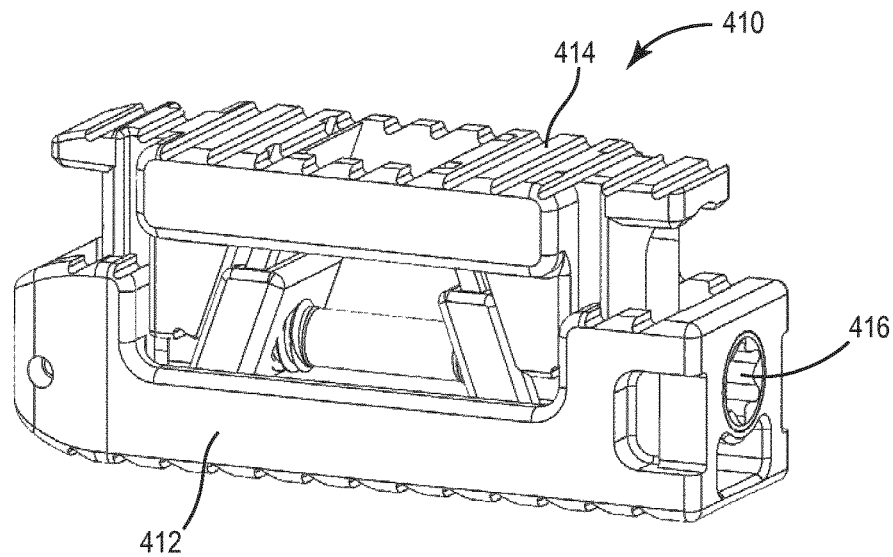
FIG. 23 is a perspective view of the implant of FIG. 19 in an expanded position according to one embodiment.
Figure 24:
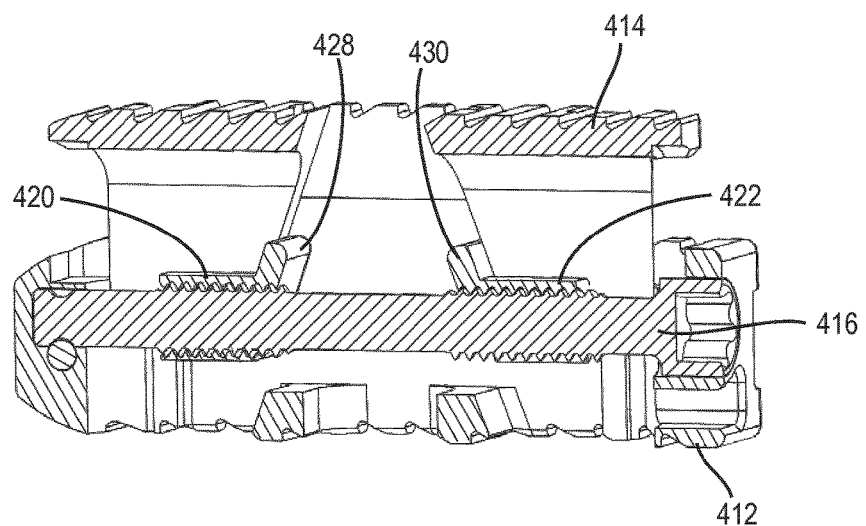
FIG. 24 is a cross-sectional view of the implant of FIG. 19 in an expanded position according to one embodiment.
Figure 25:
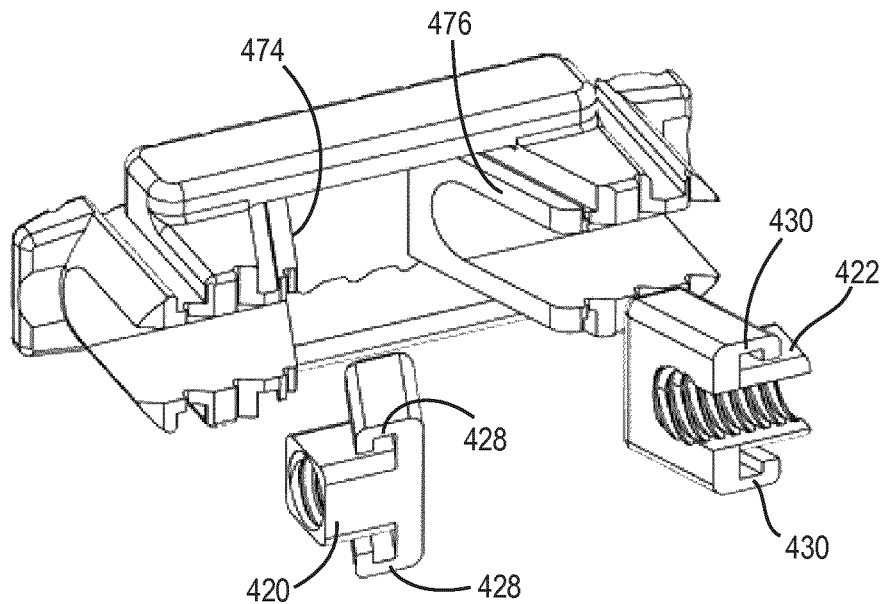
FIG. 25 is a partial exploded view of the implant of FIG. 19 according to one embodiment.
Figure 26:
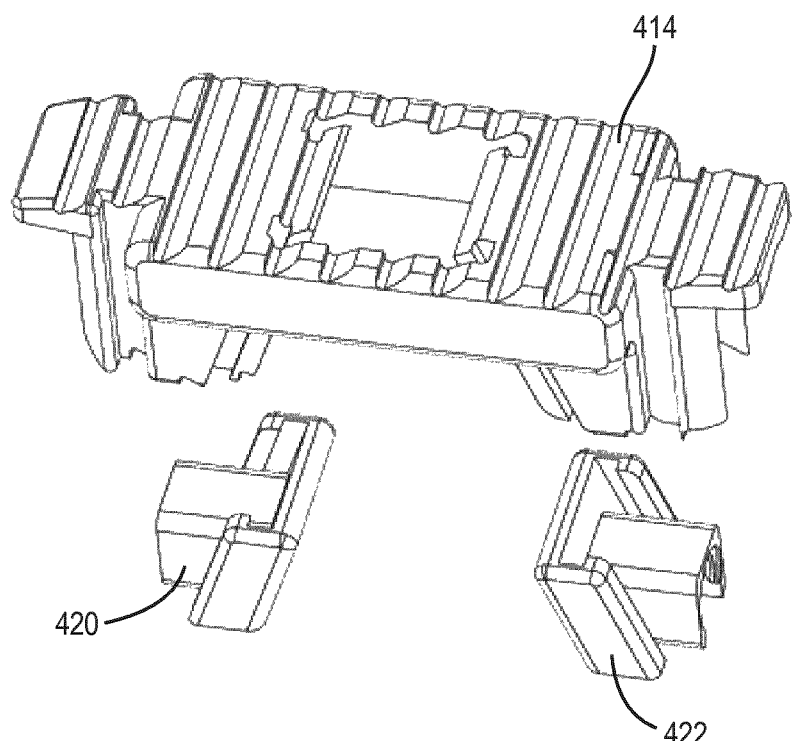
FIG. 26 is a partial exploded view of the implant of FIG. 19 according to one embodiment.

Similar to implant 10, and as shown in FIGS. 23 and 24, as the control members 420, 422 move along the control shaft 416, the control members 420, 422 further move along the control rails 474, 476, thereby causing relative movement of the adjustable member 414 and the base member 412. As the control members 420, 422 translate along the control shaft 416, the adjustable member 414 is moved due to the orientation and shape of the first and second control rails 474, 476. The rate of movement of the control members 420, 422, and therefore adjustable member 414, can be adjusted by modifying the slope of the control rails 474, 476 relative to the control shaft 416, as discussed in greater detail elsewhere herein, including FIGS. 9A-9C.

It should be noted that implant 410 may share various features with the other implants described herein, and be made of the same, similar, or different materials. For example, various components of implant 410 may be made of metal, plastic, composites, or other suitable bio-compatible materials. Further, implant 410 may be usable in connection with the spine or other parts of the body.

Referring now to FIGS. 27-34, an expandable implant 510 is shown according to an exemplary embodiment. The implant 510 is usable, for example, between and/or within vertebral bodies of the spine, and may share any or all of the features of the other inter/intra-body implants discussed elsewhere herein. All such combinations of features are to be understood to be within the scope of the present disclosure. It should be understood that the implant 510 may in some embodiments be usable in other portions of the body in addition to the spine, and all such applications are to be understood to be within the scope of the present disclosure. The implant 510 is substantially similar to implant 10, with the exception of the configuration of the control channels as discussed below.

Figure 27:
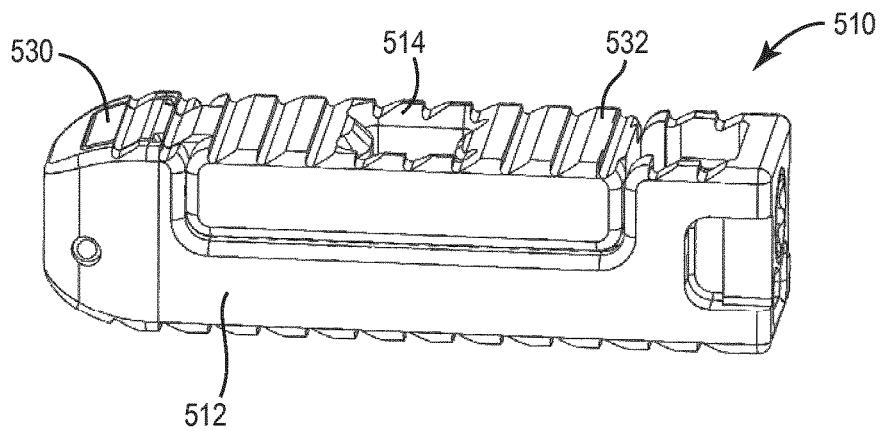
FIG. 27 is a perspective view of an implant in a collapsed position according to another embodiment.
Figure 29:
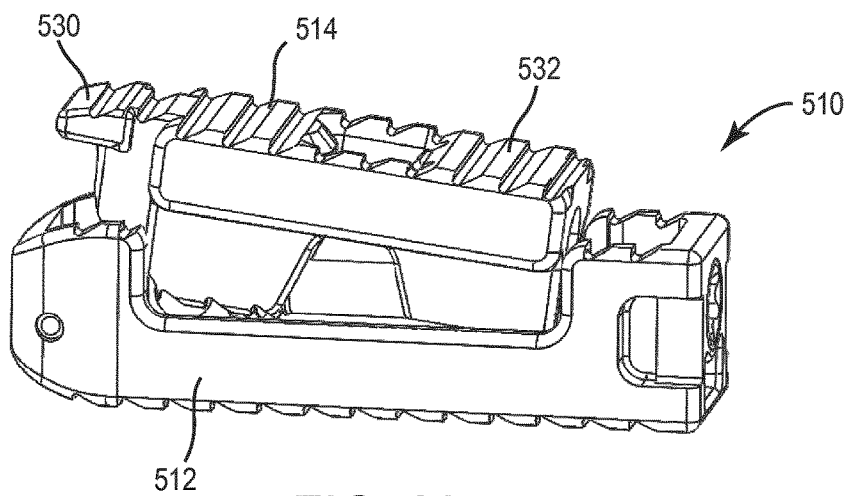
Figure 30:
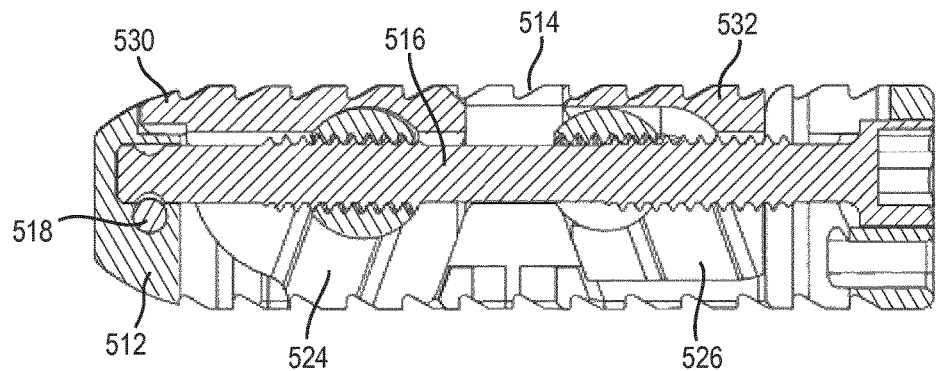
FIG. 30 is a side cross-section view of the implant of FIG. 27 in a collapsed position according to one embodiment.
Figure 32:
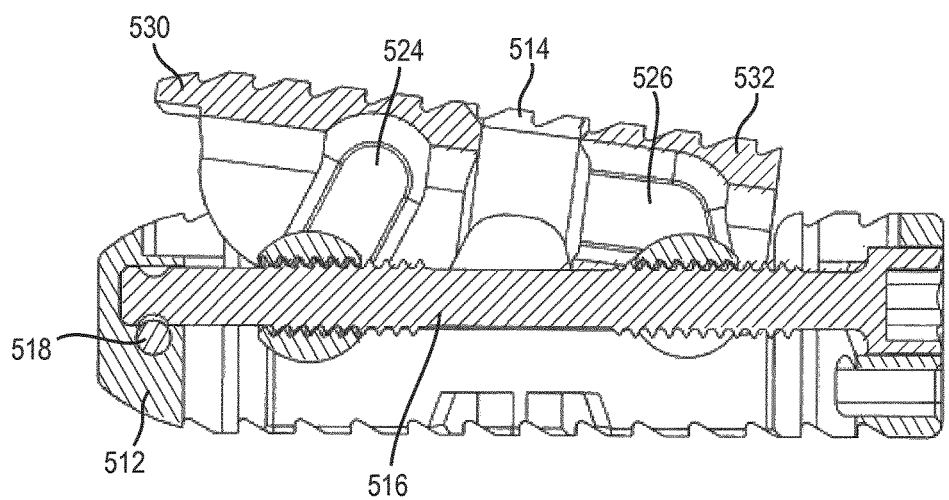
FIG. 32 is a side cross-section view of the implant of FIG. 27 in an expanded position according to one embodiment.
Figure 33:
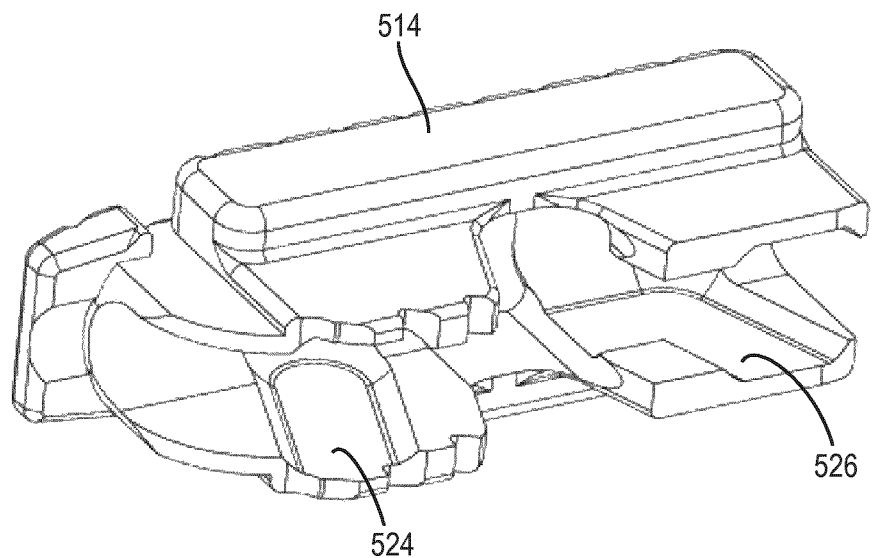
FIG. 33 is a perspective view of a portion of the implant of FIG. 27 according to one embodiment.

According to an exemplary embodiment, the implant 510 includes a base member 512 and an adjustable member 514 adjustably coupled to the base member 512. A control shaft 516 is received by the base member 512 and is retained by a retention pin 518 passing through a portion of the base member 512. A first control member 520 and a second control member 522 are received on the control shaft 516 and are movable along the control shaft 516 to adjust a position of the adjustable member 514 between a collapsed position, as shown in FIGS. 27 and 30, and an expanded position, as shown in FIGS. 29 and 32.

In one embodiment, the adjustable member 514 includes a front or first end 530, and a rear or second end 532. The adjustable member 514 further includes one or more control channels, such as a first control channel 524 and a second control channel 526. The first control channel 524 receives the first control member 520, and the second control channel 526 receives the second control member 522. In some embodiments, the control members 520, 522 are received in the control channels 524, 526 in a sliding manner such that the control members 520, 522 are able to translate within the control channels 524, 526. In further embodiments, each control channel has a shape such that the control channel surrounds the control member and at least partially corresponds in shape to the control member.

As shown in FIGS. 27-32, as the control members 520, 522 move along the control shaft 516, the control members 520, 522 further move within the control channels 524, 526, thereby causing relative movement of the adjustable member 514 and the base member 512. As the control members 520, 522 translate along the control shaft 516, the adjustable member 514 is moved based on the shape of the first and second control channels 524, 526. The rate of movement of the control members 520, 522, and therefore the adjustable member 514, can be adjusted by modifying the slope of the control channels 524, 526 relative to the control shaft 516.

Figure 34:
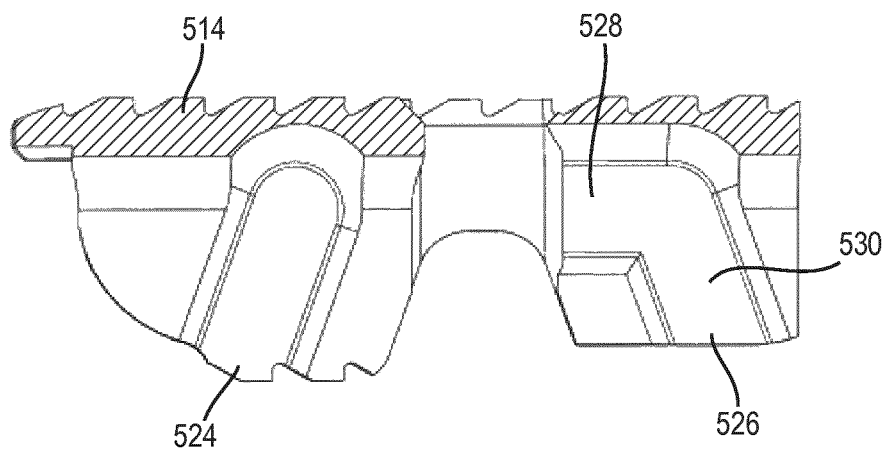
FIG. 34 is a cross-section view of the portion of the implant of FIG. 33 according to one embodiment.

For example, as shown in FIG. 34, the first control channel 524 extends at an angle relative to the control shaft 516, and has a substantially linear form and constant slope, thereby providing a generally constant corresponding rate of movement of the first end 530 of the adjustable member 514. The second control channel 526 includes a first channel portion 528 and a second channel portion 530 which extend at different angles relative to the control shaft 516. As shown in FIG. 34, the first channel portion 528 is generally parallel to the control shaft 516, and the second channel portion 530 extends at an angle similar to that of first control channel 524. As such, the second control channel 526 provides a non-constant rate of movement of second end 532 of the adjustable member 514.

Figure 28:
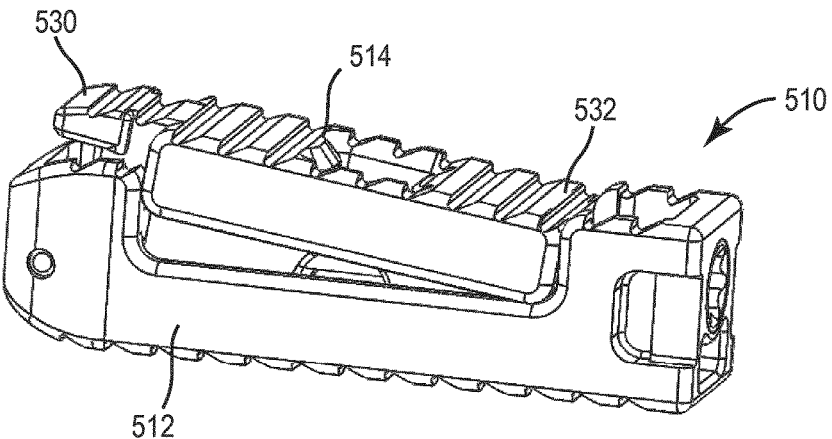
FIG. 28 is a perspective view of the implant of FIG. 27 in an intermediate position according to one embodiment.
Figure 31:
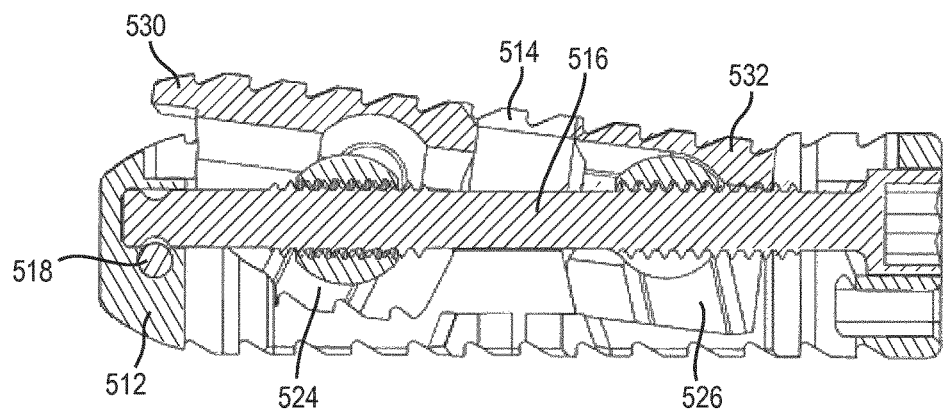
FIG. 31 is a side cross-section view of the implant of FIG. 27 in an intermediate position according to one embodiment.

FIGS. 27-32 illustrate the corresponding movement of the adjustable member 514 resulting from the differing configurations of the first control channel 524 and the second control channel 526. In FIGS. 27 and 30, the implant 510 is in a collapsed position, such that the control members 520, 522 reside in the upper/inner most positions within the first and second control channels 524, 526. FIGS. 28 and 31 illustrate implant 510 in an intermediate expanded position, where second control member 522 is positioned generally at the intersection of the first channel portion 528 and the second channel portion 530. Due to the orientation of the first channel portion 528, the second end 532 of adjustable member 514 has remained generally at the same height as that shown in FIGS. 28 and 30, while due to the configuration of first control channel 524, the first end 530 of the adjustable portion 514 has moved upward relative to the base member 512. FIGS. 29-32 show the implant 510 in a fully expanded position, where control members 520, 522 reside in the lower/outer-most positions within the first and second control channels 524, 526. Due to the angled configurations of both the first control channel 524 and the second channel portion 530 of the second control channel 526, both the first end 530 and the second end 532 move relative to the base member 512.

Providing an implant with adjustment features such as those provided by implant 510 may facilitate accommodating a desired spinal curvature or other anatomical features where non-parallel supporting surfaces are suitable for a particular application. It should be noted that the control channels and/or control rails herein may take any desired configuration to provide desired expansion and contraction characteristics for a particular implant.

Referring now to FIGS. 35-44, an expandable implant 610 is shown according to an exemplary embodiment. Implant 610 may share many of the features of the other inter/intra-body implants discussed elsewhere herein. All such combinations of features are to be understood to be within the scope of the present disclosure. Implant 610 is generally similar to the other implants disclosed herein in structure and function except that implant 610 utilizes a single control member/control channel configuration, and further utilizes a pivot pin about which an adjustable member pivots relative to a base member.

Figure 35:
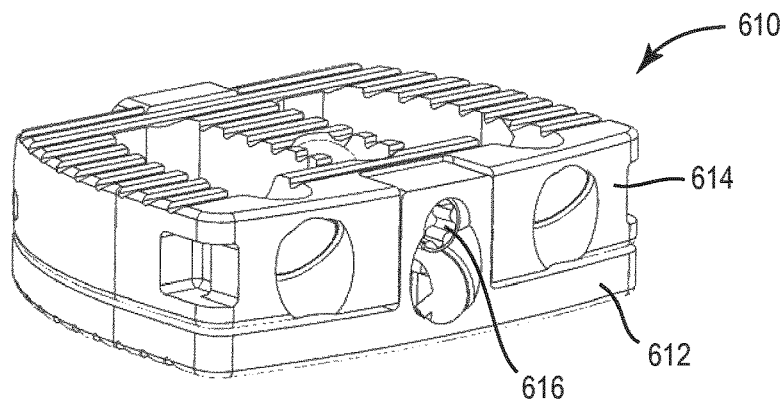
FIG. 35 is a side perspective view of an implant in a collapsed position according to another embodiment.
Figure 36:
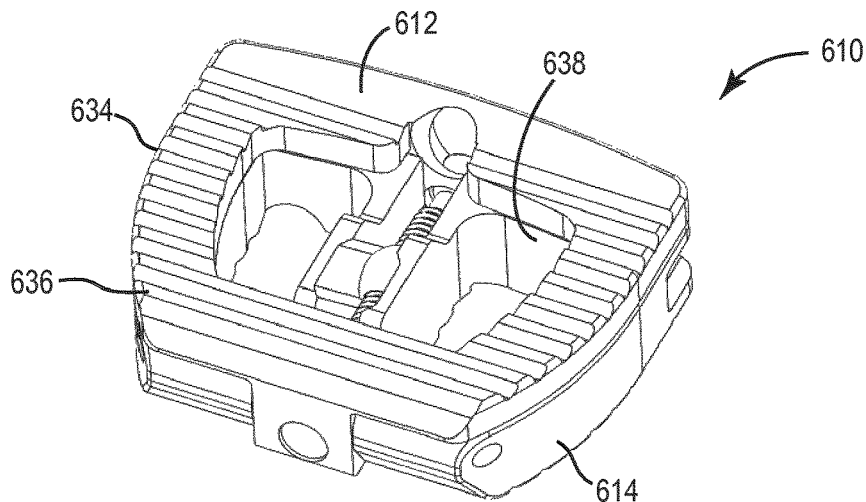
FIG. 36 is a bottom perspective view of the implant of FIG. 35 according to one embodiment.
Figure 37:
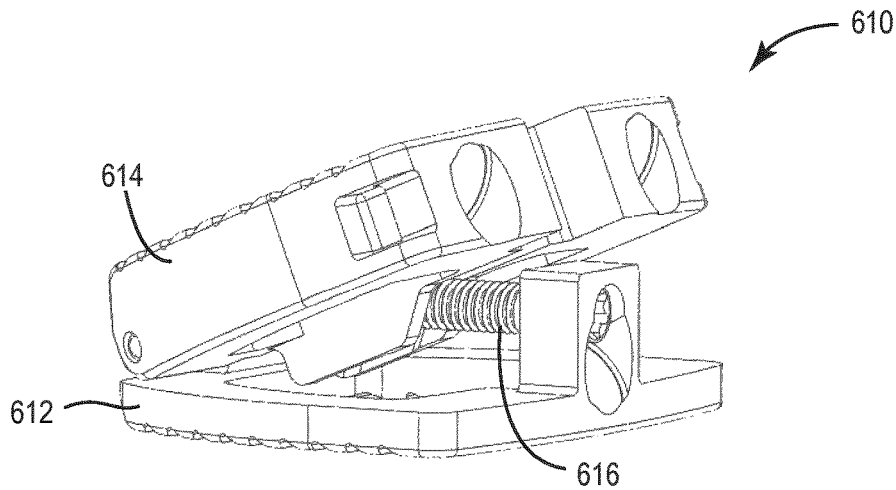
FIG. 37 is a perspective view of the implant of FIG. 35 in an expanded position according to one embodiment.
Figure 38:
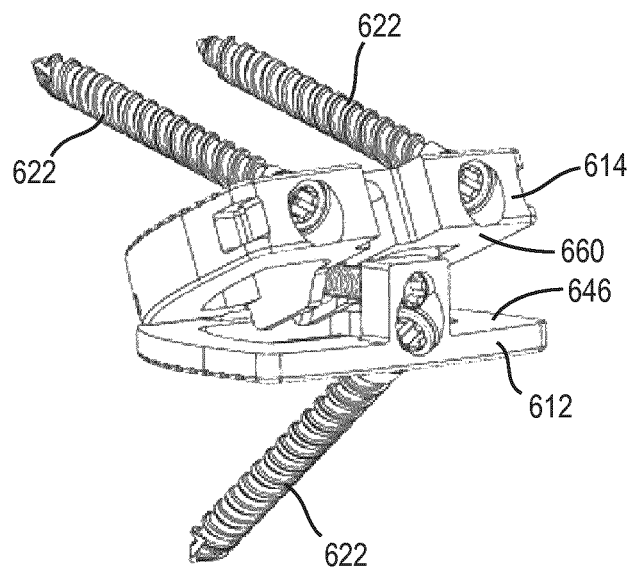
FIG. 38 is perspective view of the implant of FIG. 35 in an expanded position with bone screws according to one embodiment.

According to an exemplary embodiment, implant 610 includes a base member 612 and an adjustable member 614 adjustably coupled to the base member 612. A control shaft 616 is received by the base member 612 and is retained by a retention pin 618 (e.g., a pivot pin or member, retaining pin) passing through a portion of the base member 612 and/or the adjustable member 614. A control member 620 is received on the control shaft 616 and is movable along the control shaft 616 to adjust a position of the adjustable member 614 between a collapsed position, as shown in FIGS. 35 and 36, and an expanded position, as shown in FIGS. 37 and 38.

In one embodiment, the base member 612 includes a front or first end 624, a rear or second end 626, and a central cavity 638 disposed between the first end 624 and the second end 626. The base member 612 further includes a top surface 646 and a bottom surface 634 opposite the top surface 646 and having ridges or projections 636 formed by corresponding grooves. The projections 636 are configured to engage adjacent portions of bone. The base member 612 further includes a planar portion 628. A first extension 630 is positioned at the first end 624 and extends upward from the planar portion 628, and a second extension 632 is positioned at the second end 626 and extends upward from the planar portion 628. A pin aperture 640 extends through the first extension 630 and is configured to receive the retention pin 618 (e.g., in a press fit, sliding, or other manner). The second extension 632 includes a bone screw bore 650 configured to receive a bone screw 622. The first extension 630 includes a first control bore 642 and the second extension includes a second control bore 644. Control bores 642, 644 receive opposing ends of the control shaft 616.

Figure 43:
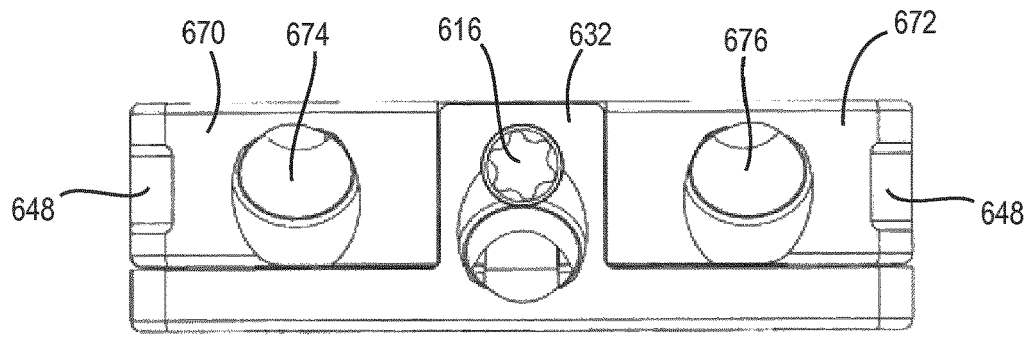
FIG. 43 is a front view of the implant of FIG. 35 according to one embodiment.
Figure 44:
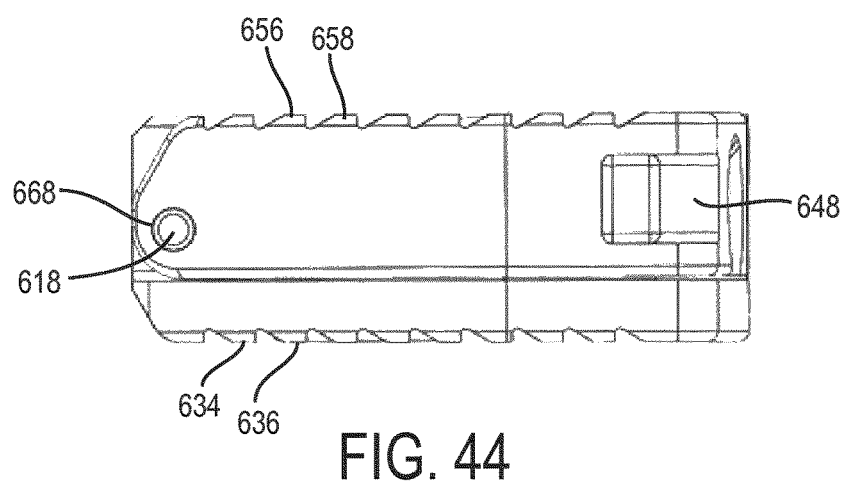
FIG. 44 is a side view of the implant of FIG. 35 according to one embodiment.

In one embodiment, the adjustable member 614 includes a front or first end 652, a rear or second end 654, and cavities 664 extending through the adjustable member 614 and positioned between the first end 652 and the second end 654. The adjustable member 614 further includes a top surface 656 having ridges or projections 658 formed by corresponding grooves, and a bottom surface 660. The adjustable member 614 further includes pin apertures 668 configured to receive the retention pin 618 to enable movement (e.g., pivoting) of the adjustable member 614 relative to the base member 612. Further, the adjustable member includes a first bone screw support portion 670 including a bone screw bore 674 and a second bone screw support portion 672 having a bone screw bore 676. As shown in FIG. 43, the first and second bone screw support portions 670, 672 of the adjustable member 614 and the second extension 632 of the base member 612 collectively form a front face of the implant 610, such that the control shaft 616 and the bone screws 622 are accessible via the front face of the implant 610 (e.g., when the implant 610 is in a collapsed position).

Figure 39:
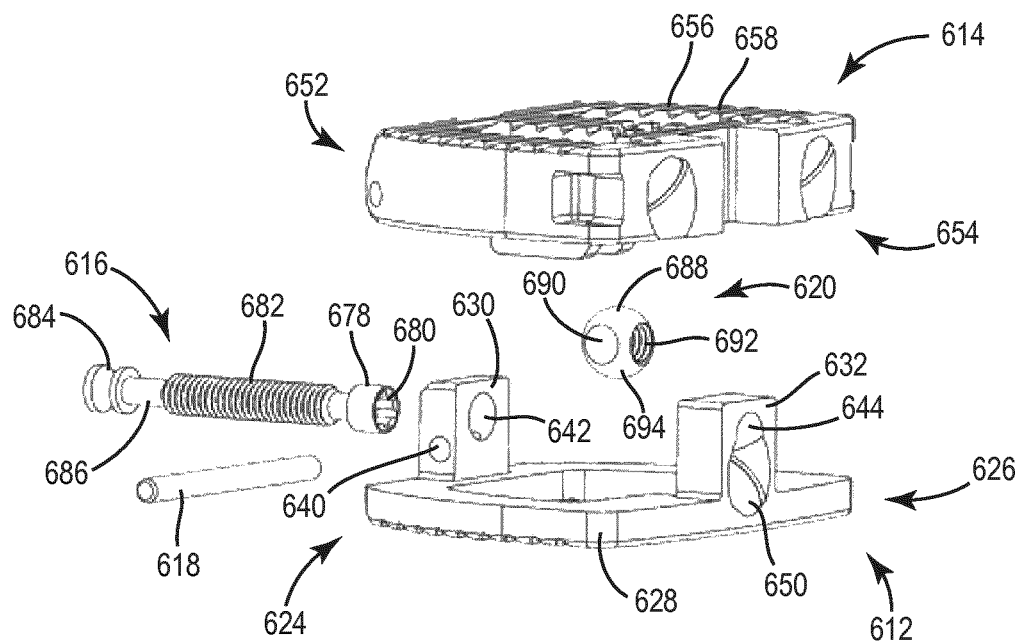
FIG. 39 is an exploded view of the implant of FIG. 35 according to one embodiment.
Figure 40:
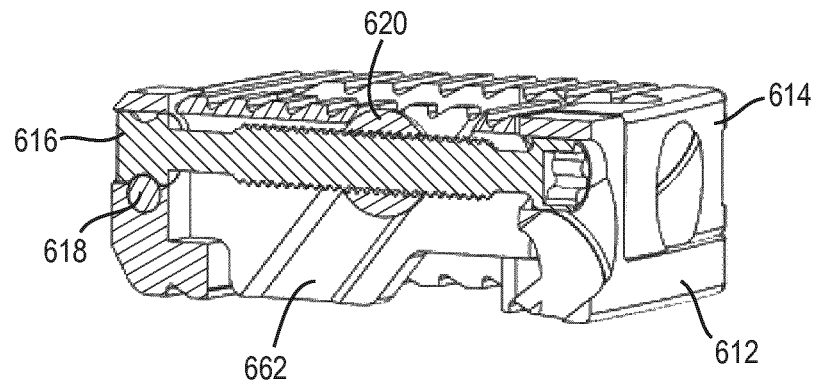
FIG. 40 is a cross-section view of the implant of FIG. 35 in a collapsed position according to one embodiment.
Figure 41:
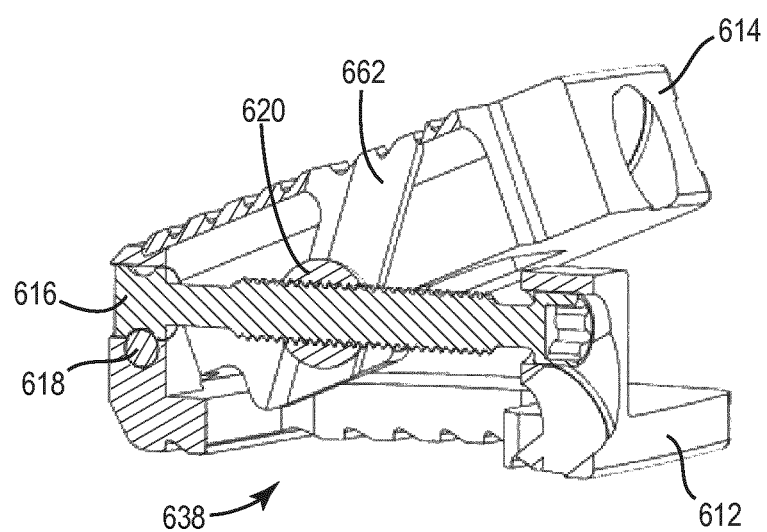
FIG. 41 is a cross-section view of the implant of FIG. 35 in an expanded position according to one embodiment.
Figure 42:
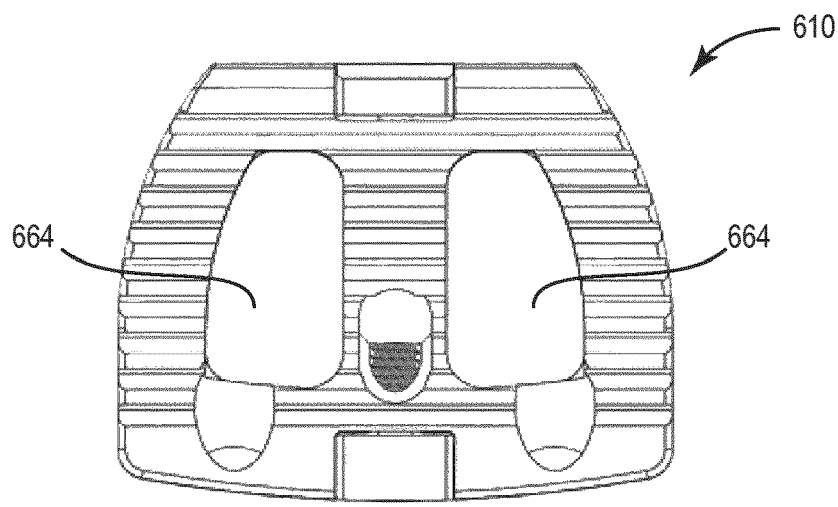
FIG. 42 is a top view of the implant of FIG. 35 according to one embodiment.

Referring to FIGS. 39-41, in one embodiment, the adjustable member 614 includes one or more control channels, such as control channel 662. The control channel 662 receives the control member 620. In some embodiments, the control member 620 is received in the control channel 662 in a sliding manner such that the control member 620 is able to translate within the control channel 662. In further embodiments, the control channel 662 has a shape such that the control channel 662 surrounds the control member 620 and at least partially corresponds in shape to the control member 620.

Referring to FIG. 39, the control shaft 616 includes a head portion 678, a tool port 680 disposed within the head portion 678, and a retention groove 684 located at an end opposite the head portion 678. In some embodiments, the control shaft 616 further includes a control thread 682. Non-threaded portions 686 may be located on one or both side of the control thread 682.

The control member 620 includes a body 688, one or more flat portions 690, and an internal thread 692. In some embodiments, the control member 620 further includes a slotted portion configured to enable passing the control member 620 over a portion (e.g., non-threaded portion 686) of the control shaft 616. The control member 620 moves or translates both along the control shaft 616 and within or on the control channel 662.

Referring to FIGS. 40-41 the control shaft 616 is received by the base member 612 such that the retention groove 684 is positioned with the first extension 630 of the base member 612 and the head portion 678 is positioned within the second extension 632 of the base member 612. In one embodiment, the control shaft 616 is rotatable within the base member 612, and the retention pin 618 extends through the first extension 630 and into the retention groove 684 of the control shaft 616 to enable rotation of the control shaft 616 while inhibiting translation of the control shaft 616 relative to the base member 612. The internal thread 692 of the control member 620 is received on the control thread 682 of the control shaft 616 such that as the control member 620 moves along the control shaft 616, the control member 620 further moves within the control channel 662, thereby causing relative movement (e.g., pivotal movement) of the adjustable member 614 relative to the base member 612 (e.g., about retention pin 618). For example, FIGS. 40 and 41 show the control member 620 moving along the control shaft 616. As the control member 620 translates along the control shaft 616, the adjustable member 614 pivots about the retention pin 618. The rate of movement of the control member 620, and therefore the adjustable member 614, can be adjusted by modifying the slope of the control channel 662 relative to the control shaft 616.

In use, implant 610 is positioned within a desired space (e.g., between adjacent portions of bone) while in the first, collapsed position, as shown in FIG. 35. To position implant 610, an appropriate tool may be used to engage tool recesses 648 and manipulate implant 610 into a desired position. Once in a desired position, a subsequent tool may be utilized to engage tool port 680 and rotate control shaft 616 to pivot adjustable member 614 to a desired degree of expansion. It should be noted that based on a particular application, the adjustable member 614 may be utilized in a fully collapsed position, a fully expanded position, or any intermediate position therebetween. One or more bone screws 622 may be screwed into adjacent portions of bone as shown in FIG. 38. Once implant 610 is properly positioned and expanded to a desired height, bone graft material may be delivered by way of, for example, apertures 664 or alternatively, by the space formed due to the expansion of adjustable member 614. The various apertures in and through the base member 612 and adjustable member 614 may in some embodiments facilitate the growth of bone material in and around implant 610 to further stabilize the device.

It should be noted that implant 610 may share various features with the other implants described herein, and be made of the same, similar, or different materials. For example, various components of implant 610 may be made of metal, plastic, composites, or other suitable bio-compatible materials. Further, implant 160 may be usable in connection with the spine or other parts of the body.

Referring now to the Figures generally, the various embodiments disclosed herein provide expandable implants including a base member, an adjustable member adjustably coupled to the base member and movable between a first, collapsed position, and a second, expanded position, and a control shaft rotatably received by the base member, where rotation of the control shaft cause relative movement of the adjustable member relative to the base member. At least one control member is received on the control shaft and by the control channel, and rotation of the control shaft causes the control member to translate along the control shaft and along the control channel.

In some embodiments, the adjustable member moves in a linear fashion relative to the base member. In other embodiments, the adjustable member moves in a non-linear fashion relative to the base member. In further embodiments, the adjustable member pivots about a pivot axis relative to the base member. The pivot axis may be provided by a pivot pin extending through one or both of the adjustable member and the base member.

In some embodiments, a single control member and control channel are utilized. In other embodiments, multiple (e.g., 2) control members and control channels are utilized. In some embodiments, the multiple control channels are parallel and straight. In other embodiments, the control channels are non-parallel and straight (e.g., angled toward each other). In further embodiments, the control channels are non-parallel and non-straight such that the adjustable member moves in a non-linear fashion relative to the base member.

In some embodiments, the control shaft includes a control thread corresponding to each control member. As such, while in some embodiments the control shaft includes a single control thread, in other embodiments the control shaft includes multiple (e.g., first and second) control threads. In some embodiments, the control threads are like-threaded. In other embodiments, the control threads have different threads. For example, in some embodiments, a first control thread is opposite-handed from a second control thread. In further embodiments, a first control thread has a different pitch from a second control thread. In yet further embodiments, a first control thread is different handed and has a different pitch from a second control thread.

In some embodiments, one or both of the adjustable member and the base member include projections/grooves to provide a gripping surface intended to facilitate gripping adjacent portions of bone. In further embodiments, one or both of the adjustable member and the base member include one or more apertures and/or cavities configured to promote bone growth in and around the adjustable member and the base member. In some embodiments, the apertures extend from a top, bottom, and/or side surface of the adjustment member or the base member and to a central cavity of the implant.

According to any of the embodiments disclosed herein, one or more bone screws may be included and positioned to extend through one or both of the adjustable member and the base member and into adjacent portions of bone. In some embodiments, multiple bone screws are used. A first bone screw may extend through the adjustable member and into a first portion of bone, and a second bone screw may extend through the base member and into a second portion of bone. In further embodiments, multiple bone screws are accessible and manipulatable by way of a front face of the implant defined by one or both of the adjustable member and the base member. A head and tool port of the control shaft may further be accessible by way of the front face of the implant.

In various embodiments, any suitable configuration of the control shaft/control member(s)/control channel(s) may be utilized. In some embodiments, an at least partially spherical control member threadingly engages a threaded control shaft and translates both along the control shaft and within the control channel. In other embodiments, the control member is non-spherical and is received at least partially on or in a control rail or control channel provided by the adjustable member, such that the control member translates along both the control shaft and the control channel or control rail.

It is important to note that the construction and arrangement of the elements of the various implants and implant components as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. An expandable implant, comprising:
a base member including a top surface, a first end, and a second end, and defining a central cavity positioned between the first end and the second end;
an adjustable member including a top surface and at least one control channel, wherein the adjustable member is adjustably coupled to the base member and movable between a first, collapsed position, and a second, expanded position;
a control shaft rotatably received by the base member, wherein rotation of the control shaft causes relative movement of the adjustable member relative to the base member; and
at least one control member received on the control shaft and by the control channel, wherein rotation of the control shaft causes the control member to translate along the control shaft and along the control channel;
wherein the control member is at least partially spherical and includes a flat portion configured to engage a corresponding flat portion on the adjustable member to prevent rotation of the control member within the control channel.

2. The expandable implant of claim 1, wherein the at least one control channel includes a first control channel and a second channel, and wherein the at least one control member includes a first control member received in the first control channel and a second control member received in the second control channel.

3. The expandable implant of claim 2, wherein the first control channel and the second control channel extend in non-parallel directions.

4. The expandable implant of claim 2, wherein the first control channel and the second control channel extend in parallel directions.

5. The expandable implant of claim 2, wherein a first axis of the first control channel defines a first angle of intersection with an axis of the control shaft and wherein a second axis of the second control channel defines a second, different angle with the axis of the control shaft.

6. The expandable implant of claim 2, wherein rotation of the control shaft causes the first and second control members to translate in opposite directions along the control shaft.

7. The expandable implant of claim 1, wherein the top surface of the adjustable member and a bottom surface of the base member define a height of the implant and are configured to engage adjacent portions of bone.

8. The expandable implant of claim 7, wherein rotation of the control member changes the height of the implant.

9. The expandable implant of claim 7, wherein rotation of the control member changes a width of the implant transversely relative to the height.

10. An expandable implant, comprising:
a base member including a top surface, a first end, and a second end, and defining a central cavity positioned between the first end and the second end;
an adjustable member including a top surface, a first control channel, and a second control channel;
a control shaft rotatably received by the base member, wherein the control shaft defines a first acute angle with the first control channel and a second acute angle with the second control channel, and wherein rotation of the control shaft causes relative movement of the adjustable member relative to the base member;
a first control member received on the control shaft and by the first control channel such that rotation of the control shaft causes translation of the first control member along the control shaft and along the first control channel; and a second control member received on the control shaft and by the second control channel such that rotation of the control shaft causes translation of the second control member along the control shaft and along the second control channel;

wherein the first acute angle is different from the second acute angle.

11. The expandable implant of claim 10, wherein the first control member is received on a first control thread of the control shaft and the second control member is received on a second control thread of the control shaft, wherein the control shaft includes a non-threaded portion between the first control thread and the second control thread.

12. An expandable implant, comprising:
- a base member including a top surface, a first end, and a second end, and defining a central cavity positioned between the first end and the second end;
- an adjustable member including a top surface, a first control channel, and a second control channel;
- a control shaft rotatably received by the base member, wherein the control shaft defines a first acute angle with the first control channel and a second acute angle with the second control channel, and wherein rotation of the control shaft causes relative movement of the adjustable member relative to the base member;
- a first control member received on the control shaft and by the first control channel such that rotation of the control shaft causes translation of the first control member along the control shaft and along the first control channel;
- a second control member received on the control shaft and by the second control channel such that rotation of the control shaft causes translation of the second control member along the control shaft and along the second control channel;
- wherein the first control member is received on a first control thread of the control shaft and the second control member is received on a second control thread of the control shaft, wherein the control shaft includes a non-threaded portion between the first control thread and the second control thread; and
- wherein the second control member includes a slot configured to enable the second control member to be transversely slid over the non-threaded portion of the control member while unthreaded from the second control thread.

13. The expandable implant of claim 12, the first acute angle is different from the second acute angle.

14. The expandable implant of claim 12, wherein the adjustable member is configured to move relative to the base member in a non-linear manner.

15. An expandable implant, comprising:
- a base member including a top surface, a first end, and a second end, and defining a central cavity positioned between the first end and the second end;
- an adjustable member including a top surface, a first control channel, and a second control channel;
- a control shaft rotatably received by the base member, wherein the control shaft defines a first acute angle with the first control channel and a second acute angle with the second control channel, and wherein rotation of the control shaft causes relative movement of the adjustable member relative to the base member;
- a first control member received on the control shaft and by the first control channel such that rotation of the control shaft causes translation of the first control member along the control shaft and along the first control channel; and
- a second control member received on the control shaft and by the second control channel such that rotation of the control shaft causes translation of the second control member along the control shaft and along the second control channel;
- wherein the base member defines a first bone screw bore configured to receive a first bone screw extending through the bottom surface of the base member, and wherein the adjustable member defines a second bone screw bore configured to receive a second bone screw extending through the top surface of the adjustable member.

16. The expandable implant of claim 15, wherein the first bone screw bore is provided in a first bone screw support portion of the base member, and wherein the second bone screw bore is provided in a second bone screw support portion of the adjustable member, wherein the first bone screw support portion and the second bone screw support portion collectively define an end surface of the expandable implant, and wherein the first bone screw, the second bone screw, and the control shaft are all manipulatable at the end surface of the implant.

17. An expandable implant, comprising:
- a base member;
- an adjustable member movably coupled to the base member and defining a first control channel and a second control channel;
- a control shaft translationally fixed and rotatably movable relative to the base member, wherein rotation of the control shaft causes relative movement of the adjustable member relative to the base member, wherein the control shaft defines a first intersection angle with the first control channel and a second different intersection angle with the second control channel;
- a first control member received on the control shaft and in the first control channel such that rotation of the control shaft causes translation of the first control member along the control shaft and within the first control channel; and
- a second control member received on the control shaft and within the second control channel such that rotation of the control shaft causes translation of the first control member along the control shaft and within the first control channel;
- wherein the adjustable member is configured to move relative to the base member in a non-linear manner.

18. The expandable implant of claim 17, wherein the first control member is rotatably fixed relative to the first control channel and the second control member is rotatably fixed relative to the second control channel.

19. The expandable implant of claim 17, wherein a cross-sectional shape of the first control channel generally corresponds to a peripheral shape of the first control member, and wherein a cross-sectional shape of the second control channel generally corresponds to a peripheral shape of the second control member.

* * * * *